US012577556B2

(12) United States Patent
Vijayan et al.

(10) Patent No.: US 12,577,556 B2
(45) Date of Patent: Mar. 17, 2026

(54) PERTURBATION BEADS FOR USE IN ASSAYS

(71) Applicant: Zafrens Inc., San Diego, CA (US)

(72) Inventors: Kandaswamy Vijayan, San Diego, CA (US); Ravi Ramenani, San Diego, CA (US); Chulmin Choi, San Diego, CA (US); Aurelien Laguerre, La Jolla, CA (US); Gopichandran Ravichandran, San Diego, CA (US); Nicholas Sam-Soon, San Diego, CA (US); Yi Zhang, San Diego, CA (US); David Milliken, San Diego, CA (US); Kenneth Chng, San Diego, CA (US); Maina Ndungu, San Diego, CA (US)

(73) Assignee: Zafrens Inc., San Diego, CA (US)

( * ) Notice: Subject to any disclaimer, the term of this patent is extended or adjusted under 35 U.S.C. 154(b) by 0 days.

(21) Appl. No.: 18/734,832

(22) Filed: Jun. 5, 2024

(65) Prior Publication Data

US 2024/0327824 A1 Oct. 3, 2024

Related U.S. Application Data

(63) Continuation of application No. PCT/US2024/032022, filed on May 31, 2024, and a continuation-in-part of application No. 18/195,049, filed on May 9, 2023.

(60) Provisional application No. 63/624,181, filed on Jan. 23, 2024, provisional application No. 63/339,782, filed on May 9, 2022.

(51) Int. Cl.
*C12N 15/10* (2006.01)

(52) U.S. Cl.
CPC ................................ *C12N 15/1065* (2013.01)

(58) Field of Classification Search
CPC ........................... C12N 15/10; C12N 15/1065
See application file for complete search history.

(56) References Cited

U.S. PATENT DOCUMENTS

| | | | |
|---|---|---|---|
| 9,638,636 B2 | 5/2017 | Tibbe et al. | |
| 10,828,643 B2 | 11/2020 | Vijayan et al. | |
| 10,981,170 B2 | 4/2021 | Vijayan et al. | |
| 11,027,272 B1 | 6/2021 | Vijayan et al. | |
| 11,040,343 B1 | 6/2021 | Mahakalkar et al. | |
| 11,084,037 B2 | 8/2021 | Vijayan et al. | |
| 11,739,440 B2 * | 8/2023 | Bell | G01N 33/5306 435/6.11 |
| 11,946,095 B2 | 4/2024 | Lam et al. | |
| 2007/0161043 A1 | 7/2007 | Nie et al. | |
| 2014/0323330 A1 | 10/2014 | Bergo | |
| 2019/0093103 A1 | 3/2019 | Vijayan et al. | |
| 2019/0210018 A1 | 7/2019 | Vijayan et al. | |
| 2020/0001295 A1 * | 1/2020 | Vijayan | C40B 50/14 |
| 2020/0243290 A1 | 7/2020 | Sax et al. | |
| 2021/0229087 A1 | 7/2021 | Zhang et al. | |
| 2021/0308668 A1 | 10/2021 | Mahakalkar et al. | |
| 2021/0402404 A1 | 12/2021 | Gutierrez et al. | |
| 2022/0235406 A1 | 7/2022 | Brower et al. | |
| 2022/0403374 A1 | 12/2022 | Soumillon | |
| 2022/0403452 A1 | 12/2022 | Lance et al. | |
| 2024/0044882 A1 | 2/2024 | Glezer | |
| 2024/0327824 A1 | 10/2024 | Vijayan et al. | |

FOREIGN PATENT DOCUMENTS

| | | | |
|---|---|---|---|
| WO | 1997043301 A2 | 11/1997 | |
| WO | 2016118915 A1 | 7/2016 | |
| WO | 2016138496 A1 | 9/2016 | |
| WO | 2019/060830 A1 | 3/2019 | |
| WO | 2020243160 A1 | 12/2020 | |
| WO | 2021042011 A1 | 3/2021 | |
| WO | WO-2021155040 A1 * | 8/2021 | B01L 3/5025 |
| WO | 2023/059935 A1 | 4/2023 | |
| WO | 2023154694 A1 | 8/2023 | |
| WO | 2024211897 A2 | 10/2024 | |

OTHER PUBLICATIONS

Icha et al., Phototoxicity in Live Fluorescence Microscopy, and How to Avoid It, Bioessays, 2017, 39(8), 1-15. (Year: 2017).*
Rickgauer et al., Simultaneous Cellular-Resolution Optical Perturbation and Imaging of Place Cell Firing Fields, Nature Neuroscience, 2014, 17(12), 1816-1827. (Year: 2014).*
Wile et al., Molecular Beacon-Enabled Purification of Living Cells by Targeting Cell Type-Specific mRNAs, Nature Protocols, 2014, 9(1), 2411-2424. (Year: 2014).*
Abali, F. (2016). Expansion of Cancer Cells in Self-Sorting Microwells.
Avital-Shmilovici, M., Liu, X., Shaler, T., Lowenthal, A., Bourbon, P., Snider, J., . . . & Collins, N. (2022). Mega-High-Throughput Screening Platform for the Discovery of Biologically Relevant Sequence-Defined Non-Natural Polymers. ACS Central Science, 8(1), 86-101.
Betterelli Giuliano, C. (2022). Development of tools for the precise control of biological parameters via microfluidics (Doctoral dissertation, Strasbourg).
Cheng, X., Wu, M., Chin, R., Lam, H., Chen, D., Wang, L., . . . & Peters, B. (2018). A simple bead-based method for generating cost-effective co-barcoded sequence reads.
Cho, C. F., Behnam Azad, B., Luyt, L. G., & Lewis, J. D. (2013). High-throughput screening of one-bead-one-compound peptide libraries using intact cells. ACS combinatorial science, 15(8), 393-400.
Delley, C. L., & Abate, A. R. (2021). Modular barcode beads for microfluidic single cell genomics. Scientific reports, 11(1), 10857.
Gokmen, M. T., & Du Prez, F. E. (2012). Porous polymer particles—A comprehensive guide to synthesis, characterization, functionalization and applications. Progress in polymer science, 37(3), 365-405.

(Continued)

*Primary Examiner* — Amy M Bunker
(74) *Attorney, Agent, or Firm* — Banner & Witcoff, Ltd.

(57) ABSTRACT

Disclosed are uniquely labeled perturbation beads used alone or in combination with a capture bead. These perturbation beads are useful in drug discovery especially in assays conducted in a mapped assay device. Such a uniquely labeled perturbation bead, when used in an examination area of a mapped assay device, allows for correlating the sequence of nucleic acids and other components from a lysed cell to the specific examination area where the nucleic acid was retrieved.

11 Claims, 10 Drawing Sheets

(56) References Cited

OTHER PUBLICATIONS

Kim, S. H., Lee, G. H., & Park, J. Y. (2013). Microwell fabrication methods and applications for cellular studies. Biomedical Engineering Letters, 3, 131-137.
Lee, S. S., Lim, J., Tan, S., Cha, J., Yeo, S. Y., Agnew, H. D., & Heath, J. R. (2010). Accurate MALDI-TOF/TOF Sequencing of One-Bead-One-Compound Peptide Libraries with Application to the Identification of Multiligand Protein Affinity Agents Using in Situ Click Chemistry Screening. Analytical chemistry, 82(2), 672-679.
Lin, G., Baker, M. A., Hong, M., & Jin, D. (2018). The quest for optical multiplexing in bio-discoveries. Chem, 4(5), 997-1021.
Lindström, S., & Andersson-Svahn, H. (2011). Miniaturization of biological assays—Overview on microwell devices for single-cell analyses. Biochimica et Biophysica Acta (BBA)—General Subjects, 1810(3), 308-316.
Macconnell, A. B., Mcenaney, P. J., Cavett, V. J., & Paegel, B. M. (2015). DNA-encoded solid-phase synthesis: encoding language design and complex oligomer library synthesis. ACS Combinatorial Science, 17(9), 518-534.
Manzoor, A. A., Romita, L., & Hwang, D. K. (2021). A review on microwell and microfluidic geometric array fabrication techniques and its potential applications in cellular studies. The Canadian Journal of Chemical Engineering, 99(1), 61-96.
Matula, K., Rivello, F., & Huck, W. T. (2020). Single-cell analysis using droplet microfluidics. Advanced Biosystems, 4(1), 1900188.
Nestler, H. P., Wennemers, H., Sherlock, R., & Dong, D. L. Y. (1996). Microautoradiographic identification of receptor-ligand interactions in bead-supported combinatorial libraries. Bioorganic & Medicinal Chemistry Letters, 6 (12), 1327-1330.
Paulick, M. G., Hart, K. M., Brinner, K. M., Tjandra, M., Charych, D. H., & Zuckermann, R. N. (2006). Cleavable hydrophilic linker for one-bead-one-compound sequencing of oligomer libraries by tandem mass spectrometry. Journal of combinatorial chemistry, 8(3), 417-426.
Price, A. K., Macconnell, A. B., & Paegel, B. M. (2016). hvSABR: Photochemical Dose-Response Bead Screening in Droplets. Analytical chemistry, 88(5), 2904-2911.
Sauter, B., Schneider, L., Stress, C., & Gillingham, D. (2021). An assessment of the mutational load caused by various reactions used in DNA encoded libraries. Bioorganic & medicinal chemistry, 52, 116508.
Stuart, T., & Satija, R. (2019). Integrative single-cell analysis. Nature reviews genetics, 20(5), 257-272.
Torres, A. J., Hill, A. S., & Love, J. C. (2014). Nanowell-based immunoassays for measuring single-cell secretion: characterization of transport and surface binding. Analytical chemistry, 86(23), 11562-11569.
Wang, Y., Cao, T., Ko, J., Shen, Y., Zong, W., Sheng, K., . . . & Weitz, D. (2020). Dissolvable polyacrylamide beads for high-throughput droplet DNA barcoding. Advanced Science, 7(8), 1903463.
Stoeckius, M., Hafemeister, C., Stephenson, W., Houck-Loomis, B., Chattopadhyay, P. K., Swerdlow, H., . . . & Smibert, P. (2017). Simultaneous epitope and transcriptome measurement in single cells. Nature methods, 14(9), 865-868.Stoeckius, Marlon, Hafemeister, Christoph, Stephenson, William, et al., “Large-scale simultaneous measurement of epitopes and transcriptomes in single cells”, Nat Methods, Sep. 2017; 14(9): pp. 865-868.
Wang, T., Liu, J., Shen, L., Tonti-Filippini, J., Zhu, Y., Jia, H., . . . & Wang, W. (2013). STAR: an integrated solution to management and visualization of sequencing data. Bioinformatics, 29(24), 3204-3210.
Johan, A. N., & Li, Y. (2022). Development of Photoremovable Linkers as a Novel Strategy to Improve the Pharmacokinetics of Drug Conjugates and Their Potential Application in Antibody-Drug Conjugates for Cancer Therapy. Pharmaceuticals, 15(6), 655.
“Invitation to Pay Additional Fees and, Where Applicable, Protest Fee” in PCT/US2024/032014—Mailed Jan. 3, 2025; Received Jan. 14, 2025.
Jan. 17, 2025—(WO) International Search Report/Written Opinion—PCT/US24/32022.
Cao, C., Dhumpa, R., Bang, D. D., Ghavifekr, Z., Høgberg, J., & Wolff, A. (2010). Detection of avian influenza virus by fluorescent DNA barcode-based immunoassay with sensitivity comparable to PCR., Analyst, 135, 337-342.
Feb. 18, 2025—(US) Non-final Office Action—U.S. Appl. No. 18/734,732.
Feb. 25, 2025—(WO) International Search Report and Written Opinion—App PCT/US24/32014.
Jun. 4, 2025—(US) Final Office Action—U.S. Appl. No. 18/734,732.
Jun. 17, 2025—(WO) International Search Report and Written Opinion—App PCT/US25/012691.
Jan. 6, 2026—(US) Non-final Office Action—U.S. Appl. No. 18/734,732.

* cited by examiner

Where B = blue, G = Green O = Orange, R = Red and Y = Yellow

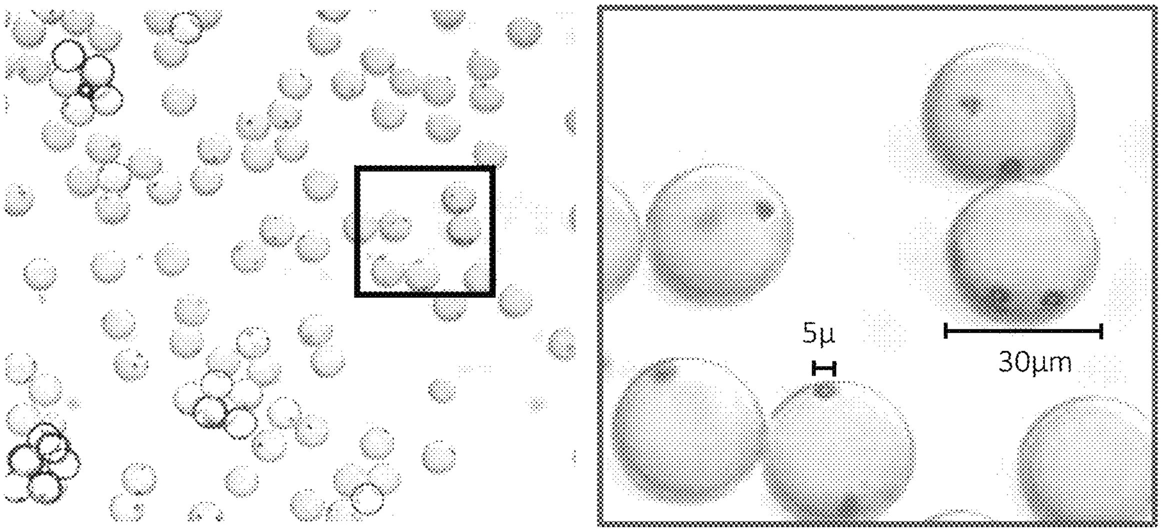
FIG. 7A
FIG. 7B
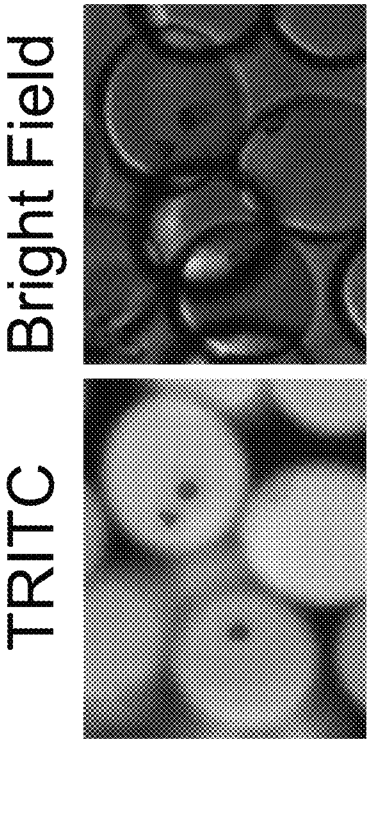
FIG. 7C
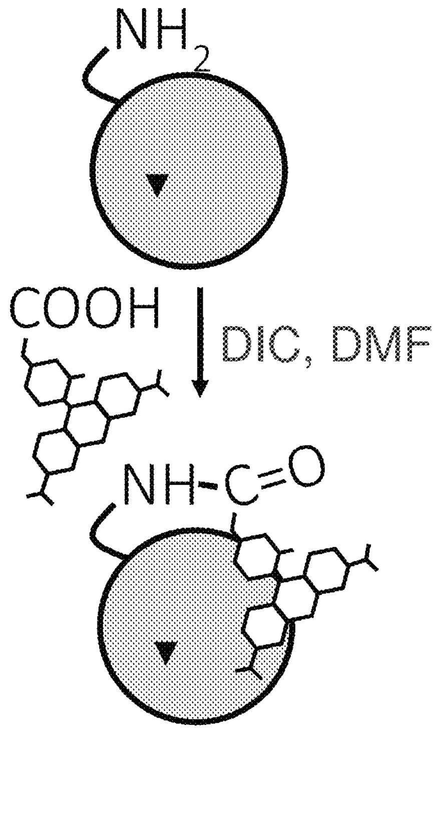

PERTURBATION BEADS FOR USE IN ASSAYS

FIELD

This disclosure provides for uniquely labeled perturbation beads used alone or in combination with a capture bead. These perturbation beads are useful in drug discovery, such as in assays conducted in a mapped assay device.

BACKGROUND

Assays conducted for a combinatorial library of compounds generated on a set of beads employ high throughput assay devices where typically the population of beads are employed in an assay device with a single bead being combined with a one or more cells in an examination area. Such assays can be conducted using combinatorial libraries having up to 5,000,000 or more individual perturbation beads each having a multiplicity of the same unique releasable perturbation element bound thereto. The assay in each examination area typically includes a perturbation element released from the perturbation bead which then perturbs the cell or cells in that examination area. After the assay is complete, it is conventional to determine the consequences that the perturbation had on the cell or cells by assessing the changes in nucleic acids expressed by the cell(s) in response to the perturbation. Protein expression changes may also be assessed by using DNA-barcoded antibodies, whereby the total nucleic acid change in response to perturbations may identify both genomic and proteomic changes ("perturbation components"). The perturbation bead also includes a releasable oligonucleotide which codes for the specific perturbation element on that bead ("perturbation oligonucleotides") which allows a technician to correlate the changes in gene and protein expression back to the perturbation element that induced such changes.

In some cases, a capture bead also can be included in the examination area. The capture bead captures perturbation oligonucleotides released from the perturbation bead as well as nucleic acids that are released from the cell after cell lysis. At the end of the assay, capture beads from each of the examination areas are preferably pooled and then the captured perturbation oligonucleotides and nucleic acids are sequenced. Using this approach, the technician will know what perturbation compound is associated with nucleic acids recovered from a lysed cell. Such knowledge is referred to herein as changes in "static functionality" as defined below as it measures consequences of the perturbation after the assay is completed.

However, since the capture beads are pooled, this approach provides no information that correlates the changes in static functionality back to a specific examination area in the assay device where the assay was performed. If such could be done, substantially more meaningful information regarding an individual assay could be combined with the changes in static functionality. These changes would include, among others, what changes in cellular functionality occurred during the assay by a given perturbation element. To do so, it is necessary to find a way that allows for recovered products from cell lysis by the capture bead to include information that codes for the specific perturbation bead and the specific examination well which contained that bead.

Stated differently, limiting the information collected from an assay solely to the structure of the perturbation element and the nucleic acids (comprising both genomic and proteomic changes via DNA barcoded antibodies) generated in response to that perturbation only provides changes at the end of the assay that are static in nature, collected at the time of capture. However, if the technician could also analyze dynamic changes in cellular functionality induced during the assay by the perturbation such as changes in cellular morphology, changes in cell surface markers including the presence of new markers or changes to or elimination of existing markers, and other such related information, such information could be combined with the changes in static functionality to provide a more complete understanding of the impact of the perturbation element on the cell.

Accordingly, there is an ongoing need to expand the amount of information retrieved from one or more of the examination areas found in an assay of a library of diverse compounds. Such additional information would expand the knowledge obtained from each assay and would facilitates drug discovery.

SUMMARY

This disclosure provides for uniquely labeled perturbation beads. This disclosure also provides for combinations of a uniquely labeled perturbation bead with a capture bead. In either case, a perturbation bead as described herein, whether used alone or in combination with a capture bead, is configured to allow for analysis of the changes in cellular functionality generated during an assay induced by exposing a cell to a perturbation element as well as the static information which is necessary to provide a more global analysis of the impact the perturbation element had on the cell.

In some embodiments, there is provided a labeled perturbation bead comprising: multiple copies of the same perturbation element releasably attached to that bead and which is unique to that bead;

an optically detectible label or set of labels that is/are unique to that perturbation bead; and multiple copies of a unique perturbation oligonucleotide releasably attached to said perturbation bead and which code for the perturbation element as well as for the unique label or combination of labels on the perturbation bead.

In some embodiments, said perturbation oligonucleotide further comprises: a first and optionally a second binding element or precursor thereof wherein said first binding element is complementary to and associates with a complementary capture binding element releasably bound on a capture bead; and said second binding element is complementary to and associates with a complementary binding element present on one or more perturbation components from a lysed cell.

In some embodiments, there is provided a second binding component or precursor thereof on the perturbation oligonucleotide which is complementary to and associates with one or more perturbation components released by a lysed cell provided that if said first binding element binds to the capture bead, then said second binding element is present and binds to a perturbation component.

In some embodiments, there is provided a population of perturbation beads each bead comprising:

a) multiple copies of the same perturbation element releasably attached to that bead and which is unique to that bead;

b) an optically detectible label or set of labels that is/are unique to each of said perturbation beads in said population; and c) multiple copies of a unique perturbation oligonucleotide releasably attached to said perturbation bead and which codes for the perturbation element as well as for the unique label or combination of labels on the perturbation bead, wherein said perturbation oligonucleotide further comprises a first and optionally a second binding component or precursor thereof wherein said first binding element is complementary to and associates with a complementary functionality releasably bound onto a capture bead or a perturbation component released from a lysed cell, and wherein said optional second binding component or precursor thereof is complementary to and associates with one or more perturbation components released by a lysed cell provided that if said first binding element binds to the capture bead, then said second binding element is present and binds to a perturbation component.

In some embodiments, said perturbation oligonucleotide further comprises a first and a second binding element or precursor thereof, wherein said first binding element is complementary to and associate with a complementary functionality releasably bound onto a capture bead or a perturbation component released from a lysed cell, and further wherein said second binding component or precursor thereof is complementary to and associates with one or more perturbation components released by a lysed cell.

In some embodiments, the perturbation oligonucleotide codes for both the perturbation element and the unique label or set of labels associated with the perturbation bead.

In some embodiments, the perturbation oligonucleotide comprises two distinct components. One component codes for the perturbation element on the bead and the other component codes for the unique label or set of labels on said perturbation bead. In some embodiments, the two components are attached to each other to form a single perturbation oligonucleotide.

In some embodiments, there is provided a perturbation bead of formula I:

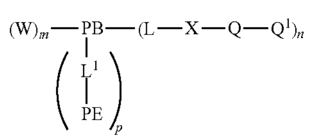

(I)

where:

W is an optically detectable label or a set of optically detectable labels that uniquely identify a perturbation bead;

PB is a perturbation bead;

PE is a perturbation element;

L is a releasable linker;

$L^1$ is a releasable linker which may be the same or different from L and when different, L and $L^1$ may be cleaved with a same stimulus or with a different stimuli;

Q is a perturbation oligonucleotide that codes for the perturbation element and the unique label or set of labels;

$Q^1$ is a binding element;

X is a bond or a binding element wherein, when X is a binding element, it can be the same or different from $Q^1$;

m is an integer from 1 to 100 (or more, depending on a size of the bead and/or label, for example), wherein m denotes the number of distinguishable optically detectable labels bound to the perturbation bead;

n represents a number (e.g., a multiplicity) of such (L-X-Q-$Q^1$) groups bound to the perturbation bead; and p represents a number (e.g., a multiplicity) of such (PE) groups bound to the perturbation bead.

In some embodiments, L and $L^1$ are cleaved using the same stimulus. When both are cleaved, the assay solution will contain a multiplicity of PE and a multiplicity of the group represented by formula II:

$$X\text{-}Q\text{-}Q^1 \quad (II)$$

where X, Q and $Q^1$ are as defined above. In some embodiments, provided herein is an oligonucleotide represented by formula II.

In some embodiments, there is provided a capture bead can be employed in the assay and would have a structure such as found in formula III:

$$CB\text{-}(L^2\text{-}CE)_s \quad (III)$$

where CB is a capture bead, CE is a capture element on CB, $L^2$ is a releasable linker that links a multiplicity of a capture element, CE to CB, and s represents the number of such groups in that multiplicity. In such a case, one of X and $Q^1$ is a complementary binding element to CE whereas the other of X and $Q^1$ can bind perturbation components (PCs) recovered from the lysed cell. The resulting structures of the capture bead after such binding are represented by formulae IV and V:

$$CB\text{-}(L^2\text{-}CE\text{-}X\text{-}Q\text{-}Q^1)_{s'}, \quad (IV)$$

and $$CB\text{-}(L^2\text{-}CE\text{-}Q^1\text{-}Q\text{-}X)_{s'}, \quad (V)$$

based on which of X and $Q^1$ is complementary to CE and s' being the bound fraction of s.

In some embodiments, X is a binding element, which can be different from that of $Q^1$.

In some embodiments, $Q^1$ is a complementary functionality to a capture bead binding element, CE, and X is binding element to a perturbation component released from a lysed cell. In other embodiments, X is a complementary functionality to a capture bead binding element, CE, and $Q^1$ is binding element to a perturbation component released from a lysed cell.

In some embodiments, X has a complementary functionality to a perturbation component.

In some embodiments, n, p, s and s' range from $1\times10^5$ to $6.02\times10^{17}$.

In some embodiments, for each of the n L-X-Q-$Q^1$ groups, $Q^1$ can be a same capture element or different capture elements. In some embodiments, for each of the n L-X-Q-$Q^1$ groups, X can be a same capture element or different capture elements. Such same or different capture elements can include, by way of example only, a complementary oligonucleotide strand, avidin, streptavidin, biotin, an antibody, a binding portion of an antibody, an enzyme, an enzyme binding domain, a substrate for an enzyme or enzyme binding domain, and the like.

In some embodiments, when X is a binding element and X-Q-$Q^1$ is released from the perturbation bead in the absence of a capture bead, there is provided an oligonucleotide that is obtained by cleavage of the releasable linker, L, and after lysing of the cell that is represented by formula VI:

$$PC^1\text{-}X\text{-}Q\text{-}Q^1\text{-}PC^2 \quad (VI)$$

where X, Q, and $Q^1$, are described as above and $PC^1$ and $PC^2$ are independently perturbation components, PC as described above, that can be the same or different as each other.

In some embodiments, the perturbation element in each of the above embodiments is a multiplicity of the same compound that is unique to each bead.

In some embodiments, the perturbation oligonucleotide comprises at its distal and/or proximal end relative to the perturbation bead a X and a $Q^1$ group which comprise a chain polynucleotide having repeating units of up to 2,000 guanine units, or cytosine units, or adenine units, or thymine units. In some embodiments, X and $Q^1$ are different.

In some embodiments, the perturbation oligonucleotide comprises at its proximal end a chain polynucleotide having up to 2,000 units of cytosine or guanine and at its distal end relative to the bead up to 2,000 units of thymine.

In some embodiments, the perturbation oligonucleotide comprises poly-thymine (Poly-T) having at either its distal or proximal end relative to the perturbation bead an avidin, streptavidin or biotin group.

In some embodiments, there is provided a combination of a perturbation bead and a capture bead, wherein said combination comprises:

a perturbation bead as described in formula I above; and a capture bead comprising multiple copies of a same capturing element releasably bound thereto;

wherein said combination of said perturbation bead and said capture bead is included in a register that memorializes the combination;

provided that:

a) if said perturbation bead comprises a unique label or set of labels, then said label or labels are coded by a unique oligonucleotide which is incorporated into or onto the perturbation oligonucleotide; and b) if the perturbation oligonucleotide does not code for said label or labels, then the perturbation bead further comprises a label oligonucleotide which codes for said label or labels and said label oligonucleotide is releasably attached to said perturbation bead and said released label oligonucleotide and said perturbation oligonucleotide are attachable to each other.

In some embodiments, the label oligonucleotide is reversibly bound to the perturbation bead and terminates at either end with a capture element with a poly-G or poly-C oligonucleotide; whereas the perturbation oligonucleotide is reversibly bound to the bead and terminates at one end in a poly-T oligonucleotide capture element and at the other end with a poly-C or poly-G oligonucleotide such that upon release of both oligonucleotides with their binding element (s), the label oligonucleotide will hybridize with the perturbation oligonucleotide thereby providing a continuous oligonucleotide having the label oligonucleotide and the perturbation oligonucleotide in a single strand while retaining the poly-T oligonucleotide for capturing the nucleic acids released from the lysed cells.

In some embodiments, the captured nucleic acids are m-RNA.

In some embodiments, the captured nucleic acids are mRNA and nucleic-acid barcodes attached to antibodies bound to proteins in the fixed or lysed cells.

In some embodiments, there is provided a combination which comprises a single perturbation bead as described herein and a single capture bead in at least a plurality of examination areas of a mapped assay device, wherein each of said single perturbation beads comprises a label or set of labels that is unique to that bead wherein the bead is coded by an oligonucleotide releasably bound thereto, and, said capture bead comprises multiple copies of a same capturing element releasably bound thereto, and further wherein a register of said specific perturbation bead located in each of the populated examination areas has been recorded to memorializes the specific perturbation bead to that specific examination area.

In some embodiments, the optically detectable label or set of optically detectable labels are selected from images, codes, shapes, colors, inducible colors, lettering, numbering, symbols, bar codes, universal product code (UPC) codes, quantum dots (QDs), light emitting diodes (LEDs), and materials introduced onto the perturbation bead, or combinations thereof.

In some embodiments, the perturbation oligonucleotide codes for each of the reaction steps used in the synthesis of the perturbation compound in a split-pool protocol as described herein. In some embodiments, during each step of the split-pool synthesis, a unique label is attached to each of the beads in each of the reaction vessel such that the fully extended oligonucleotide codes for both the compound that is attached to that bead as well as the unique code associated with the bead.

In some embodiments, each oligonucleotide strand coding a reaction step in each vessel comprises from about 6 to about 2,000 individual nucleotides; preferably from about 100 to about 2,000 nucleotides; and more preferably from about 800 to about 1,500 nucleotides.

In some embodiments, the capturing element is an oligonucleotide.

In some embodiments, the oligonucleotide capturing element on the capture bead attaches a complementary capturing element on the perturbation oligonucleotide by hybridization.

In some embodiments, the perturbation oligonucleotide comprises one or more capture elements or can be modified to comprise an additional capture element. In some embodiments, one of the capture elements on the perturbation oligonucleotide is complementary to the capture element on the capture bead. In some embodiments, the other capture element on the perturbation oligonucleotide is orthogonal to the capture element on the capture bead.

In some embodiments, the attachment of the perturbation oligonucleotide including capture element(s) is/are either direct or through a linker.

In some embodiments, the linker is a releasable linker.

In some embodiment, the capture element is not an oligonucleotide. In some embodiments, the capture element is a receptor or ligand for the perturbation component to be captured. Such receptors include antibodies or antibody binding fragments for the perturbation compound; an enzyme or enzyme receptor for the perturbation component, a receptor for a given cytokine or chemokine, and the like.

In some embodiments, the capturing element on the capture bead is avidin/streptavidin that captures perturbation components or the perturbation oligonucleotide that has been modified to contain an avidin group. For example, the distal terminal end of the perturbation oligonucleotide could include biotin and at its proximal end a poly-T oligonucleotide capture element at its other end; whereas the capture bead could have avidin or streptavidin as part of its capture element. Upon release of the biotin-perturbation oligonucleotide-poly-T from the perturbation bead, a tight complex is formed between avidin and biotin at one end of the perturbation oligonucleotide leaving the other end with a poly-T binding element available to bind to nucleic acids.

In some embodiments, the capturing element is poly-T.

In some embodiments, there is provided a library or register comprising a recitation of each label or set of detectable labels that code for a specific perturbation bead and the specific examination area in the assay device for each perturbation bead.

In some embodiments, there is provide a method for correlating each perturbation bead found a single examination area in a mapped assay device having a plurality of examination areas each comprising a single perturbation bead which method comprises:

a) coding each of said perturbation beads with an optically detectable label or a set of optically detectable labels unique to that bead and wherein each of said perturbation beads comprises a multiplicity of perturbation compounds wherein both the structure of the perturbation compounds and the structure of the unique label or labels is coded onto or into a perturbation oligonucleotide;

b) associating each unique labeled perturbation bead to each examination area in said device; and c) memorializing each position of each perturbation bead to the specific examination area on the mapped assay device.

In some embodiments, the correlation is done with an image aligning each of the optically detectible capture beads to a site on the map.

In some embodiments, the optically detectable labels can be a micro-component embedded in and/or attached to the perturbation bead and/or in the examination area. The micro-component can include additional information that is related to the assay to be conducted in that examination area. The additional information includes, by way of example only, the conditions of the assay, the change in functionality of the cell during the assay, the synthetic reactions used in at least one step of the compound synthesis, the identity of one or more reaction conditions used during synthesis, the technician conducting the assay, the date of the assay, the pH of the assay solution, or combinations thereof. The unique optically detectable label on each of said perturbation beads in each examination area can be recorded by photography, videography, bar codes, QR codes, and the like.

In some embodiments, such additional information can be included on the perturbation bead by a micro-component added to the examination area. Such micro-components coded with such additional information are described in U.S. patent application Ser. No. 18/195,049, entitled "High Throughput Single Cell Based Assay for Capturing Genomic Information for Functional and Imaging Analysis and Methods of Use", filed May 9, 2023, which claims benefit to U.S. provisional patent application Ser. No. 63/339,782, filed May 9, 2024; International patent application Serial No. PCT/US24/23594, entitled "Cell Transfer Component for Multi-Well Assay Device", filed Apr. 8, 2024, and/or U.S. provisional application Ser. No. 63/494,621, U.S. Provisional application Ser. No. 63/494,628 and U.S. provisional application Ser. No. 63/494,636, all filed on Apr. 6, 2023. Each of these applications are incorporated by reference herein in their entirety.

In some embodiments, the micro components can be of different shapes, same shapes but different colors or different images such as different descriptions, barcodes, messages, QR codes, and the like placed thereon, In some embodiments, different micro-components are used in combination. In some embodiments, the different images are included on the same micro component such that the combination of such images provides for a unique micro component. See, for example, FIG. 5C, where the micro component contains 4 quadrants each containing an image such as a drawing, written information, etc. The combination of these images is unique to that micro component.

In some embodiment, the unique micro component or combination of unique micro components provide(s) for a unique image that is uniquely associated with a given examination area. In some embodiments, each micro component used has a multiplicity of the same unique oligonucleotide strand associated therewith. In some embodiments, the unique strand is reversible attached to the micro component.

In some embodiments, the linker is used in combination with a unique perturbation bead. In some embodiments, the linker is reversibly attached to the micro component using a linker which is released in an orthogonal manner to the linkers used on the perturbation bead.

In some embodiments, the perturbation oligonucleotide on the perturbation bead codes only for the structure of the compound synthesized thereon. In some embodiments, the perturbation oligonucleotide comprises a bind element at its distal end. In some embodiments, the oligonucleotide strands on the micro components can have a complementary oligonucleotide binding element bound thereto that allows for hybridization to the binding element on the perturbation oligonucleotide.

In some embodiments, a single micro component having a unique label or set of labels thereon has a unique oligonucleotide strand that codes for the label and which is attached to the micro component by a cleavable linker with is cleaved in an orthogonal manner to the linker or linkers used on the bead. In a preferred embodiment, the oligonucleotide strand coding for such a micro component comprises a binding element that is complementary to a binding element on the distal end of the perturbation oligonucleotide such that upon release, the oligonucleotide strand from the micro component will hybridize to the binding element at the distal end of the perturbation oligonucleotide.

In some embodiment, multiple micro components are used such that the combination of these micro components is unique to an examination are on an assay device. In some embodiments, the oligonucleotide strands on the micro component are capable of being hybridized to the perturbation oligonucleotide by use of unique combinations of binding elements on each component or by use of orthogonally cleaved linkers such that the oligonucleotide strands can be released and hybridized to the perturbation oligonucleotide in a sequential manner.

In some embodiments, the micro components described above can be used in combination with a labeled or partially labeled perturbation bead that encodes or partially encodes for the compound synthesized thereon. In some embodiments, one or more steps of the reaction sequence used to synthesize the compound is/are coded by the micro component or a combination of micro components. In some embodiments, the unique set of micro components provides information regarding the reaction conditions and the like as described above.

In some embodiments, the unique micro component or combination of micro components are memorialized by photography or videography to correlate the examination areas where each unique micro component or combination of micro components are found. In some embodiments, the photography or videography is memorialized digitally.

Still further, the unique label or set of unique labels on said perturbation bead can be further compiled into said library thereby providing a complete set of information allowing the technician to correlate the perturbation bead to the specific examination area. Further, the perturbation component captured by the bead will be identified as originating from the specific perturbation bead by the perturbation oligonucleotide that codes for the perturbation element and the unique label or labels. In turn, the correlation between the detectable label(s) and the examination area through the map will identify the examination area used with that capture bead. This allows for tracking the captured perturbation component back to the perturbation oligonucleotide and then to the label coded thereby which identifies the specific examination area from where it originated as well as to identify the perturbation element that induced the perturbation.

In some embodiments, the capture bead can be represented by formula VII:

$$(V)_r\text{-CB-}(L^4\text{-}X^1\text{-}Q^2)_b \quad \text{(VII)}$$

where CB is a capture bead, $L^4$ is a releasable linker, b represents the multiplicity of such ($L^4$-$X^1$-$Q^2$) groups bound to the bead, $Q^2$ is a capture element, $X^1$ is a bond or a second capture element that may be the same as or different from $Q^2$, and V is optionally a unique label, or a set of unique labels and r is an integer from 0 to 100 (or larger, based on the label and a size of the CB, for example).

When r is zero and $X^1$ is a bond, the capture bead represented by formula VIII:

$$\text{CB-}(L^4\text{-}Q^2)_b \quad \text{(VIII)}$$

In some embodiments, in Formula VIII, when $X^1$ is a binding element, the attachment of $Q^2$ to $X^1$ can be direct to each other or through a linker (not shown). Each of the capturing elements, $Q^2$ and $X^1$ (when present) can be the same or different. In some embodiments, one of $Q^2$ and $X^1$ is an oligonucleotide comprising a complementary functional group to the complementary functionality on the perturbation oligonucleotide. In some embodiments, the other of $Q^2$ and $X^1$ is a functional group that is complementary to one or more of the perturbation components of the lysed cell.

In some embodiments, for each instance of b, $Q^2$ can be the same or a different capture element as in other instances. In some embodiments, the capturing element, $Q^2$, on the capture bead can contain a poly-C strand and the perturbation oligonucleotide can contain a poly-G strand. In some embodiments, the capture element on the capture bead is capable of capturing a complementary functionality on the perturbation oligonucleotide which, in turn, has a further capturing element at the opposite terminus of the perturbation oligonucleotide.

In some embodiments, b ranges from $1\times10^1$ to $6.02\times10^{17}$.

In some embodiments, the perturbation oligonucleotide codes only for the perturbation element and a label oligonucleotide codes only for the label or set of labels that uniquely define the perturbation bead. Each of these two labels is either attached to each other on the bead or are separately attached to the perturbation bead. In some embodiments, the perturbation oligonucleotide can have a capture element at one end designed to capture the label nucleotide having a complementary capture element and, at the other end, a capture element that is complementary to a perturbation component. In such a case, the perturbation bead can be represented by formula IX and/or X:

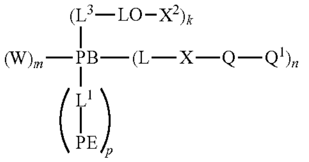
(IX)

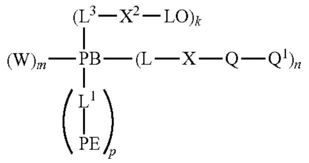
(X)

where L, $L^1$, PE, Q, $Q^1$, X, m, n, and p are as defined above, LO is a label oligonucleotide, $X^2$ is a complementary functionality to either $Q^1$ or X, $L^3$ is a releasable linker, and k represents a multiplicity of the same $L^3$-LO-$X^2$ group and ranges from $1\times10^5$ to $6.02\times10^{17}$.

In some embodiments, $L^3$ is orthogonal to both L and $L^1$ such that LO-$X^2$ can be released while retaining both PE and L-X-Q-$Q^1$ on the bead. In this embodiment, the $X^2$ group of LO-$X^2$ will attach to $Q^1$ thereby providing for in situ attachment of the label oligonucleotide to the perturbation oligonucleotide, Q, by forming a (L-X-Q-$Q^1$-LO-$X^2$) oligonucleotide.

In some embodiments, L and $L^3$ are released with the same stimulus (and optionally $L^1$) thereby allowing $X^2$ to attach to either X or $Q^1$ which forms X-Q-$Q^1$-$X^2$-LO or LO-$X^2$-X-Q-$Q^1$. When X, $X^2$ and $Q^1$ are oligonucleotides, and the perturbation component is also an oligonucleotide, then the entirety of either group is an oligonucleotide that can be sequenced.

In some embodiments of the formulas depicted above, the first binding element can be a poly-C group on the perturbation oligonucleotide and the binding element on the capture bead can be a poly-G group linked to the capture bead by a cleavable group. The second binding element on perturbation oligonucleotide can be a poly-T group. So, when released, the poly-C group on the perturbation oligonucleotide will hybridize to the poly-G group on the capture bead leaving an orthogonal poly-T binding element at the distal end of the perturbation oligonucleotide. This poly-T group will then hybridize with the poly-A functionality found on the nucleic acids released by cell lysis thereby providing an oligonucleotide that when sequenced will provide the relevant information regarding the structure of the perturbation element, the unique label on the perturbation bead, and the identity of the nucleic acids released by cell lysis. In some embodiments the poly-T binding groups on the capture bead may be replaced by complementary sequences to nucleic acids of interest present within a cell, for instance complementary sequences for specific regions in the T-cell receptor sequence (TCR) or B cell receptor sequence (BCR).

In some embodiments, the identity of the unique label or set of labels on the perturbation bead can be ascertained by sequencing the resulting nucleic acid comprising the following formulas XI and XII:

$$PC^1\text{-}X^1\text{-}Q\text{-}Q^1\text{-}PC^2 \quad \text{(XI)}$$

$$PC^1\text{-}X^2\text{-LO-X-Q-}Q^1\text{-}PC^2 \quad \text{(XII)}$$

where LO, X, Q, $Q^1$ are as defined above and $X^1$ and $X^2$ are independently binding elements. $PC^1$ and $PC^2$ denote different types of perturbation components released from the cells, for instance mRNA or proteins. In some embodiments $PC^1$ and $PC^2$ may denote similar/same perturbation components.

In some embodiments, formula XI is the result of the appropriately timed release of cleavable groups L and $L^1$ in formula I followed by hybridization then lysing of the cell which releases perturbation components $PC^1$ and/or $PC^2$ (such as mRNA) which are captured by $Q^1$. In some embodiments, formula XII is the result of the appropriately timed release of cleavable groups L, $L^1$ and $L^3$ in formula IX or X followed by hybridization then lysing of the cell which releases perturbation components $PC^1$ and/or $PC^2$ (such as mRNA) which are captured by $Q^1$ and/or $X^1/X^2$ again by hybridization. In formula XI, $Q^1$ and $X^1$ are interchangeable as to what binds $PC^1$ and/or $PC^2$. In formula XII, $Q^1$ and $X^2$ are also similarly interchangeable.

This then allows the technician to assess the specific perturbation bead corresponding to said label and, then using the register recited above, the exact examination area from which that bead was located. Taken together with visualization of the assay in that examination area (video or pictures) allows for the dynamic functionalities, features and effects of the cell in the examination area observed in that visualization before and/or after perturbation to be correlated to the static functionality (e.g., mRNA expressed and captured by the capture elements) determined by sequencing.

Still further, since each oligonucleotide sequenced will be self-identifying to the particular perturbation bead and the particular examination area, and the technician can merely pool all of the capture beads used in the assay. Once pooled, cleaving the releasable bond between the capture bead and the capture element attached thereto will release capture elements many of which will contain the oligonucleotide described above (some will be capture element free of such oligonucleotides). Since the oligonucleotides formed by hybridization to the capture bead followed by hybridization of the perturbation nucleic acids are self-identifying, pooling of all of the capture beads becomes routine.

In some embodiments, there is provided a capture bead that self-identifies a unique perturbation bead from a population of perturbation beads which capture bead comprises a multiplicity of capture elements having bound to at least a portion thereof a perturbation oligonucleotide that codes for a perturbation element and a unique label associated with a particular perturbation bead wherein said code self-identifies said unique perturbation bead from a population of uniquely labeled perturbation beads.

In some embodiments, there is provided a method for identifying a specific examination area associated to a perturbation component released from a perturbed lysed cell in said examination area of an assay device comprising a multiplicity of said examination areas, which method comprises:

a) conducting an assay in each of a multiplicity of examination areas in a mapped assay device wherein each of said examination areas comprise a cell in an assay solution;
b) including in each of said examination areas:
    i) a perturbation bead which comprises a multiplicity of perturbation elements releasably bound thereto, an optically detectable label or a set of optically detectable labels attached to said bead which uniquely identifies that bead wherein said bead comprises a multiplicity of the same perturbation oligonucleotide which is unique to said perturbation bead and is attached to thereto through a releasable linker wherein said perturbation oligonucleotide codes for the structure of the perturbation element on said bead and the unique label associated with that bead further wherein said perturbation oligonucleotide comprises one or more capture elements; and
    ii) a capture bead comprising a multiplicity of one or more capture elements releasably bound to said bead wherein at least one of the capture elements are complementary to at least one of the capture elements on the perturbation oligonucleotide provided that the perturbation oligonucleotide or the capture bead comprises at least two capture elements thereon or can be modified to include a second capture element;
c) correlating and memorializing the unique optically detectable label or set of labels in each examination area by associating the unique optically detectible labels on said capture bead to said mapped assay device thereby providing for a 1:1 relationship between each capture bead in each of the examination areas;
d) inducing a perturbation on said cell by releasing at least a portion of the perturbation element from the perturbation bead thereby inducing a functional change in said cell which comprises at least a change evidenced by one or more perturbation components expressed by said cell;
e) releasing at least a portion of the perturbation oligonucleotide from the perturbation bead for capture by the capture element on the capture bead;
e) lysing said cell to release said perturbation components into said assay solution and capturing at least one of said components onto a capture element of said perturbation oligonucleotide or said capture bead;
g) sequencing the oligonucleotide comprising the capture element, the perturbation oligonucleotide and one or more perturbation components;
h) identifying the structure of the perturbation element and the unique label or set of labels that identify the unique perturbation bead; and
i) correlating said label to a specific examination area in said mapped assay device by reference to the memorialized position of each uniquely labeled bead thereby identifying the particular examination area from which the perturbation component was retrieved.

In some embodiments, the method provided above further comprises:

j) obtaining images of each of the examination areas during the assay;
k) correlating the images to the specific examination area defined in g) above;
l) evaluating changes in cellular morphology during the assay as a result of the perturbation of the cell; and
m) combining the information obtained from sequencing in h) above with the information in l) above to provide a detailed analysis from l) above.

In some embodiments, a single unique label is associated with the perturbation bead.

In some embodiments, a set of labels is used which set comprises multiple members which, in combination, uniquely identifies the perturbation bead to which they were initially bound.

In some embodiments, there is provided a population of perturbation beads as defined above wherein each perturbation bead in said population is uniquely correlated by a label or a set of labels attached thereto as well as an oligonucleotide which correlates to the perturbation bead. In some embodiments, the oligonucleotide identifying the label also identifies the structure of the perturbation element on said bead. In some embodiments, the oligonucleotide identifying the unique label is attached to or incorporated into the perturbation oligonucleotide.

In some embodiments, the perturbation element is selected from compounds, antibodies, immune cells, siRNA, viruses, bacteria, fungi, change in one or more the conditions of the assay such but not limited to buffers, salts, pH, temperature, nutrients, oxygen levels, oxidizing agents, physical stress, and the like. In some embodiments, the perturbing element is a compound released from a perturbing bead.

In some embodiments, the capture bead is positioned in the examination area before, during, or after completion of the assay.

In some embodiments, the capture bead described above is isolated from the examination area prior to removal of the oligonucleotides from the bead.

In some embodiments, the capture bead is added to the examination area prior to the assay. In some embodiments, the capture bead is added to the examination area during the assay.

In some embodiments, there is provided a register for a given assay device which register contains a record for each unique set labels for each perturbation bead, the specific examination area where said perturbation bead is located in the assay device, and the unique perturbation oligonucleotide (including those having label information attached thereto or incorporated therein.

In some embodiments, the register comprises one or more digital photographs that record the code associated with each examination area and the optically detectable label on the perturbation bead.

In some embodiments, the digital photography uses megapixels wherein the record for each examination area comprises a different set of pixels from the other examination areas.

BRIEF DESCRIPTION OF THE DRAWINGS

FIGS. 7A-7D show examples of beads labeled with micro components that correspond to compounds attached to the beads (e.g., perturbation compounds).

DETAILED DESCRIPTION

Figure 1A:
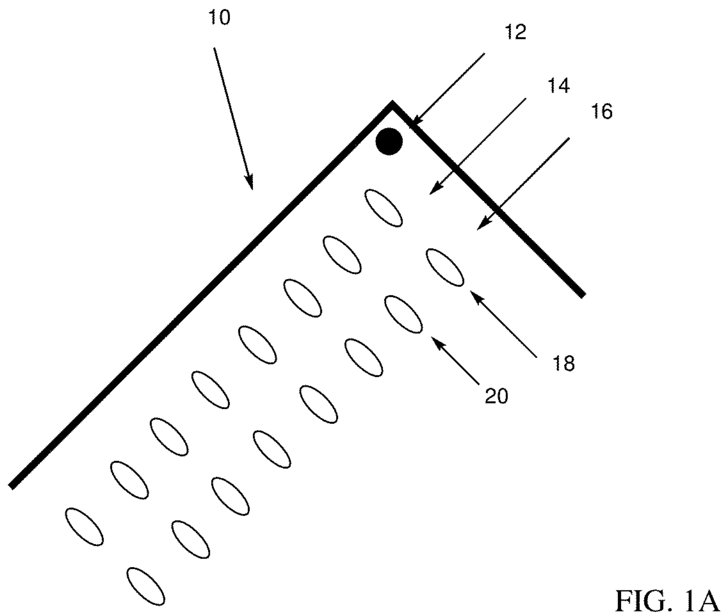
FIGS. 1A and 1B illustrate two different mapped assay devices having an orientation component.

This disclosure provides, in part, for a perturbation bead that is suitable for use in an assay device which is configured to correlate the perturbation bead to a specific examination area in the device as well as correlating any captured nucleic acid or other cellular components generated during the assay and captured as above.

1. TERMINOLOGY

In order to provide clarity to the reader, the following terms are described. Terms that are not defined have their scientifically accepted definition.

As used herein, the singular forms “a”, “an” and “the” are intended to include the plural forms as well, unless the context clearly indicates otherwise.

As used herein, the term “about” when used before a numerical designation, e.g., temperature, time, amount, concentration, and such other, including a range, indicates approximations that may vary by (+) or (−) 10%, 5%, 1%, or any subrange or a sub value therebetween. In some embodiments, the term “about” when used with regard to a dose amount means that the dose may vary by +/−10%.

As used herein, the term “comprising” or “comprises” is intended to mean that the compositions and methods include the recited elements, but not excluding others.

As used herein, the term “consisting essentially of” when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed disclosure.

As used herein, the term “consisting of” shall mean excluding more than trace elements of other ingredients and substantial method steps. Embodiments defined by each of these transition terms are within the scope of this disclosure.

In addition, the following chemical/biology and related terminology is used:

a. assay device and mapped assay device;
b. associates therewith;
c. capture bead;
d. capture element or binding element;
e. cell;
f. cellular morphology;
g. change in functionality;
h. complementary functionality;
i. compound
j. detectible labels
k. examination area;
l. label oligonucleotide;
m. linker and cleavable linker;
n. multiplicity of perturbation beads;
o. multiplicity of perturbation elements (or compounds);
p. multiplicity of oligonucleotides and capture elements;
q. oligonucleotide;
r. oligonucleotide strand;
s. optically detectible;
t. or a precursor thereof,
u. perturbation bead;
v. perturbation compound;
w. perturbation component;
x perturbation element;
y. perturbation oligonucleotide;
z. releasably attached; and
aa. unique.

The meaning of these terms as used herein is provided below (in non-alphabetical order). Terms not included in the above list that are used herein have their accepted scientific meaning.

As used herein, the term "oligonucleotide strand" refers to oligonucleotides having from about 6 to about 20,000 nucleotides or from 16 to 50,000 nucleotides. Such strands can be attached to each other to form an oligonucleotide.

As used herein, the term "oligonucleotide" refers to an oligonucleotide having from about 6 to about 500,000 nucleotides provided that if the oligonucleotide comprises 2 or more oligonucleotide strands attached together, then the oligonucleotide comprises from about 12 to about 500,000 individual nucleotides. It is understood that if an oligonucleotide is intended to be attached to another oligonucleotide, such is referred to as an oligonucleotide strand, as above. If, however, the oligonucleotide is to be used and/or discussed as a standalone component, then it is not referred to as a strand.

As used herein, the term "perturbation bead" or "PB" refers to the bead that comprises multiple copies of the same perturbation element, as defined herein, which is releasably bound to the perturbation bead. In addition, each perturbation bead further comprises a unique detectable label or set of detectable labels which uniquely identifies that bead from a population of other uniquely labeled perturbation beads as well as a perturbation oligonucleotide which codes for all or part of the perturbation element on the bead. In some embodiments, the perturbation oligonucleotide can also code for a unique label or set of labels associated with a given bead. For example, the perturbation bead may be of formulae I, IX or X.

In some embodiments, the perturbation bead may not carry a perturbation element as the perturbation is generated by physical changes such as pH, temperature, the presence or absence of nutrients, constitutes one or more conditions of the assay as noted above or, alternatively, the perturbation element can be a virus, an antibody, or a cell such as an immune cell. However, to identify the impact of such a perturbation on the nucleic acids released from a lysed cell, a uniquely labeled perturbation bead is required in order to correlate a particular perturbation bead back to a specific examination area. In such a case, the perturbation bead used is represented by the formula XIII:

$$(W)_m\text{-PB-}(L\text{-}X\text{-}Q^*\text{-}Q)_n \quad \text{(XIII)}$$

where each of W, PB, L-X, $Q^1$, m and n are as defined above and Q* is a label oligonucleotide.

Multiple perturbation beads can be used in a single examination area. For example, a first perturbation element is released from a first perturbation bead and then a second perturbation element is released from a second perturbation bead where the two perturbations are intended to separately perturb a cell, or a first perturbation element is intended to perturb the second perturbation element and then the second now perturbed perturbation element is evaluated for its impact on the cell.

As used herein, the term "label oligonucleotide" or "LO" refers to an oligonucleotide coding for the unique label or set of labels. A label oligonucleotide may be added to the perturbation bead in a situation when the perturbation oligonucleotide codes only for the perturbation element (e.g., not the label) and/or in a situation when the perturbation bead does not comprise a discrete perturbation element (e.g., Q* in formula XIII). In some embodiments, the label oligonucleotide can become bound to the perturbation oligonucleotide either on the perturbation bead, on the capture bead or in the solution phase.

As used herein, the term "capture bead" or "CB" refers to a bead used in an assay to capture the perturbation oligonucleotide which, in turn, directly or indirectly captures one or more cellular components after perturbing the cell and then lysing the cell to release such cellular components that are generated due to the perturbation ("perturbation components"). In some cases, the perturbation components include nucleic acids such as mRNA, tRNA, DNA, and the like. In some cases, the perturbation components can be chemokines, cytokines, enzymes, proteins, glycoproteins, peptides, hormones, metabolites, protein complexes, protein-nucleic acid complexes, endogenous cellular ligands, and the like. One or more capture beads can be included in an examination area. Multiple capture beads can be used when different perturbation components are to be captured. Alternatively, a single capture bead is used such that different perturbation components are to be captured by that bead.

In some embodiments, when the capture beads include a unique detectible label or a set of detectible labels associated therewith, the capture bead does not include any oligonucleotide indices that code for the unique label or set of labels on the capture bead.

In some embodiments, a single capture bead and a single perturbation bead are employed in each examination area. In some embodiments, multiple capture beads and a single perturbation bead are employed in each examination area. In some embodiments, a single capture bead and multiple perturbation beads are employed in each examination area.

As used herein, the term "detectible labels" refers to any source of information that can be detected by visual, chemical, biological, audio or other means to evidence the presence of the information generated by the label. In some cases, the detectible label is a "optically detectible label" which contains, generates or can be stimulated to generate a visual or optically detectible image/signal such as a color, visible light, lettering, numbers, symbols, barcodes, fluorescence, particles, micro-components such as microchips, UPC codes, tags, light emitting diodes (LEDs), or combinations thereof that can be seen with an unaided eye or by use of instrumentation such as a microscope or a fluorometer and the like. In some cases, the optically detectible label generates chemically or biologically induced and optically detectible signals optionally requiring suitable instrumentation to visualize such as bioluminescence. Such detectible labels include quantum dots, fluorescence (e.g., fluorescent particles, mass spectra, nuclear magnetic spectra (e.g., $H^1$ or $C^{13}$ spectrum), and the like. In some cases, the detectible label is an oligonucleotide such as siRNA, and the like. In some cases, the detectible signal generates an audio or electromagnetic signal such as those generated by an radio frequency identification device (RFID), WiFi or a Bluetooth device. The particular detectible label or labels used in the embodiments disclosed herein is within the skill of the art being dependent on the constraints of the assays to be conducted and the need to uniquely identify a component or components in that assay. Combinations of different labels can be used.

As used herein, the term an "examination area" or "area" is a defined point (e.g., region, position, space, well, compartment etc.), in an assay device or portion of an assay device, where a single assay is performed at a given time. Multiple examination areas are employed in one or more assay device. Examination areas may include droplets, wells, channels, and the like. Each area is configured to contain at least one cell, at least one capture bead, and at least one perturbation element in isolation from other areas and/or sets of areas (e.g., other locations on the assay device). In some embodiments, examination areas do not include points within a device that do not participate in an assay. That is to say that only those areas where an assay is conducted are deemed to be "examination areas" as discussed herein.

In some embodiments, a single capture bead and a single perturbation bead is employed in each examination area. In some embodiments, multiple capture beads and a single perturbation bead are employed in each examination area. In some embodiments, a single capture bead and multiple perturbation beads are employed in each examination area. In some embodiments multiple capture beads and multiple perturbation beads are employed in each examination area.

As used herein, the term "perturbation oligonucleotide" or "PO" (sometimes referred to as Q in the formulas) refers to an oligonucleotide which uniquely codes for all or part of the perturbation element on the perturbation bead. In some embodiments, the perturbation oligonucleotide also codes for the unique label or set of labels on the perturbation bead, thereby uniquely identifying the perturbation bead. The perturbation oligonucleotide further comprises a complementary binding domain to the binding element on the capture bead. The complementary binding domain may be preferably either the proximal or distal portion of the perturbation oligonucleotide. In some embodiments, the perturbation oligonucleotide still further comprises or can be modified to comprise a complementary binding domain to the perturbation components released from the lysed cell. In some embodiments, the perturbation oligonucleotide is attached to the perturbation bead in a releasable manner. See, for example, U.S. Provisional Patent Application Ser. No. 63/624,167 and U.S. Provisional Patent Application Ser. No. 63/542,760, which are related to coding and/or partial coding by a perturbation oligonucleotide. These applications are incorporated herein by reference in their entirety.

In some embodiments, the perturbation oligonucleotide simultaneously codes for the perturbation element as well as the unique label or set of labels on the perturbation bead. In some embodiments, the number of reaction steps required to form the perturbation compound exceeds the number of labels that are required to provide for a unique set of labels. In such cases, the perturbation oligonucleotide still simultaneously codes for both the perturbation compound and the unique set of labels as the skilled artisan would know that labeling stopped at a given step in the synthesis.

As used herein, the term "unique" means that the likelihood of duplication of, e.g., a single bead having the given label, is less than 1 in 1,000; or, in some embodiments, less than 1 in 10,000; or, in some embodiments, less than 1 in 100,000.

For example, in a split pool reaction scheme illustrated herein, a population of 100,000 beads can be split into 10 groups of approximately 10,000 beads each and then placed into separate reaction vessels. In a 6-step split-pool reaction scheme, step 1 will provide for 10 sets of beads each set with different labels. When pooled together, mixed to a homogenous mixture, and split again into 10 reaction vessels in step 2, the probability that a bead will be found in the same reaction vessel in step 2 as in step 1 is 10%. So, after step 2, the probability that beads will have the same two labels is now down to 1,000 for each reaction vessel or an aggregate of 10,000 duplications. Steps 3, 4, and 5 will likewise have a 10% probability of beads having been in the same reaction vessel throughout the steps 1 to 5. Hence, for step 3, the probability is 10% of step 2 (10,000) or 1,000 out of 100,000. For step 4, that becomes 100 beads with the same likelihood of having duplicate labels, and for step 5, that number becomes 10 out of 100,000; and step 6, the probability is 1 out of 100,000. If desired, a step 7 and step 8 would reduce the number to less than 0.01 out of 100,000. At any point, after step 5, the limited probability of duplication has been reduced to the point that the overwhelming number of such beads are unique.

In some embodiments, the presence of a duplicates can act as a control for the assay as such duplicates should provide the same results.

As used herein, the term "perturbation element" or "PE" refers to any source that perturbs a cell. Such sources include, by way of example only, peptides, compounds (e.g., drug-like small-molecules), antibodies, immune cells, siRNA, viruses, bacteria, fungi, a change in one or more the conditions of the assay such but not limited to buffers, salts, pH, temperature, nutrients, oxygen levels, oxidizing agents, physical stress, and the like. In some embodiments, the perturbing element is a compound released from a perturbation bead. Such a compound is sometimes referred to as a "perturbation compound" herein.

As used herein, the term "compound" or "perturbation compound" is an example of a perturbation element and refers to small molecules (having a molecular weight of less than about 15,000 Dalton), peptides and/or oligonucleotides that are synthesized bound to a perturbation bead through a releasable (cleavable) bond that is located between the compound and the bead. When the perturbation element is a compound on a perturbation bead that comprises multiple copies of the same compound releasable from the bead and multiple copies of a perturbation oligonucleotide which identifies the structure of or the identity of the compound, or the synthetic steps used to make the compound, the perturbation element is sometimes combined with the term "perturbation bead".

As used herein, the term "perturbation component", "perturbation product" or "PC" (or "$PC^i$" for integer i) refers to cellular components that are likely to be altered in quantity, expression, localization, identity, or other property upon exposure to a perturbation element. Such perturbation components may include mRNA, DNA, epigenetic modification, alternatively spliced mRNA, cytokines, chemokines, protein levels, protein isoforms, pre-mRNA, metabolites, lipids, glycoproteins, secreted proteins and other such components that make up a cell. Embodiments of perturbation components as mRNA are primarily discussed herein for simplicity of explanation. However, any perturbation component (e.g., proteins, metabolites, etc., as listed previously) that can be represented by a nucleic acid barcode sequence may be used in addition to, or in place of mRNA as the nucleic acid perturbation components of this disclosure. Nucleic acid barcode sequences attached to antibodies or aptamers may be used to monitor protein levels and/or metabolite levels, with the antibodies or aptamers selected to bind to the target protein or metabolite of interest, and the barcode specific to the target protein or metabolite of interest. See, e.g., Stoeckius, M., et al. (2017). Large-scale simultaneous measurement of epitopes and transcriptomes in single cells. Nature methods, 14(9), 865. The nucleic acid barcodes representing the various perturbation components may be captured similar to mRNA as disclosed herein, e.g., via poly-A sequences on the barcodes hybridizing to poly-T segments as capture elements on the beads, or via other complementary sequences to other capture elements. In embodiments of this disclosure, perturbation components from a cell are analyzed after exposure of the cell to a perturbation element and after capture of the perturbation component on a capture-beads (or in some embodiments after capture on a perturbation beads). In some embodiments, different types of perturbation components may be analyzed simultaneously.

In such embodiments, the different and/or different types of perturbation components are denoted by $PC^1$, $PC^2$, and the like, to represent the diversity of perturbation components and/or types of perturbation components.

As used herein, the term "assay device" refers to a device having a multiplicity of examination areas for conducting assays using the perturbation beads as described herein.

As used herein, the term "mapped assay device" refers to any assay device where the examination areas can be identified by the geometry of the device (e.g., X and Y coordinates or any orientation that allows the individual examination areas to be identified such as triangular shapes, trapezoidal shapes, etc.) or by images, lettering, numbering, etc. associated with each examination area such that the examination area can be uniquely identified. In some cases, a mark or label or other indicia on the assay device to allow the technician to properly orient the mapped assay device.

As used herein, the term "multiplicity of perturbation beads" means more than one bead, such as at least 90 beads, or at least 1,000 beads, or at least 10,000 beads, or at least 100,000 beads. An upper limit of beads in all cases can be as many of 5,000,000 beads or more but generally is about 2,000,000.

As to the term "multiplicity" when used in conjunction with perturbation elements, oligonucleotides, binding elements, and the like means that there is a sufficient number of each to perturb a cell, to capture perturbation components from a lysed cell, and to assess the identity of the perturbation components as well as the perturbation element that generated the perturbation components, and the examination area from which the perturbation components were generated. In some embodiments, such a multiplicity ranges from about $1\times10^9$ to about $6.02\times10^{17}$.

As used herein, the term "releasably bound thereto" or "releasably attached thereto" means that the specific component so described is attached to another component such as a bead in a releasable manner such that release/cleavage of at least a portion (meaning, e.g., 50 out 100 are released instead of half of an element is released) of such compounds, oligonucleotides or nucleic acids from the bead can be initiated (e.g., by the technician) at an appropriate (e.g., desired, scheduled or controlled) time in the assay. Such controlled releasability is achieved, in one instance, by using a cleavable covalent bond—a bond that is cleaved under appropriate stimulation from light (e.g., UV light), heat, pH change, electromagnetic stimulation, sound, salt, change in oxidation, enzymatic activity, and the like. Such cleavable bonds are well known in the art.

As used herein, the term "cellular morphology" refers to any one or a combination of two or more properties of a cell or components thereof such as the size, shape, structure, and/or form of a cell or components thereof. Cellular components are well known in the art and include the nucleus, the mitochondria, and ribosomes.

As used herein, the term "change in functionality" of a cell refers to one or more changes in cellular morphology as well as changes in the cellular expression of nucleic acids, chemokines, cytokines, enzymes, peptides, hormones and the like as compared to the cell prior to exposure to the perturbation element. Other changes in functionality include the generation of apotoptic or other biological markers by the cellular perturbation. Such apoptotic markers include chromatin condensation, blebbing, DNA fragmentation, and the like in the cell some of which can be readily visualized.

As used herein, the term "cell" refers to a eukaryotic or prokaryotic cells. In some embodiments, the cell is a bacterial or yeast cell. In some embodiments, the cell is a primary cell or cell line for use in an assay. In some embodiments, the cell is a fish cell, amphibian cell, reptilian cell, avian cell, or mammalian cell. In some embodiments, the cell is, for example, a mammalian cell, such as a cell from a primate. In some embodiments, the cell is a human cell.

Figure 2:
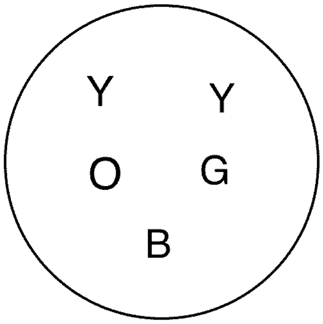
FIG. 2A-2D illustrates perturbation beads (circle) comprising a set of optical labels attached thereto that uniquely identify each capture bead from other capture beads.
Figure 2B:
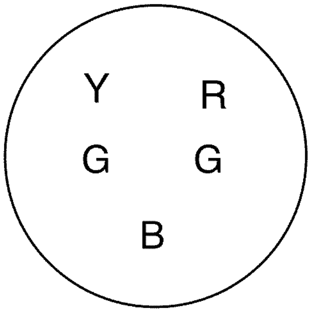
Figure 2:
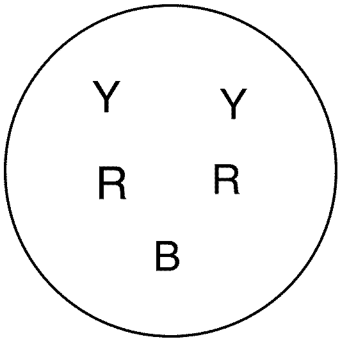
Figure 2D:
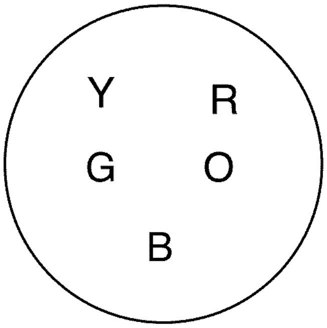

As used herein, the term "linker" refers to group which attaches one entity to another. Such a linker releasable or non-releasable. In some embodiments the linker is nucleotide or an oligonucleotide having from 1 to 2,000 nucleotide units. In some embodiments, the oligonucleotide incorporates an uracil (U) group which is cleaved by the User enzyme. In some embodiments, the oligonucleotide can be cleaved by a restriction enzyme. In some embodiments, the oligonucleotide is cleaved by a nicking enzyme. In some embodiments, CRISPR® technology is used to cleave the oligonucleotide. Chemical linkers such as carbonate, ester, carbamate groups can be cleaved by pH, esterases, lipases, and the like. Photocleavable linkers are well known in the art and include coumarin groups, ortho-nitrobenzyl groups, and others found in FIG. 2 of Johan, et al., Pharmaceuticals (Basel), 15(6):655 et seq. (June 2022) which is incorporated herein by reference in its entirety. The selection of a suitable linker is not critical and is well known to the skilled artisan.

In some embodiments, when the linker is a non-nucleotide or oligonucleotide, then it comprises at least one and up to about 40 non-hydrogen atoms including carbon, nitrogen, oxygen, sulfur, and phosphorus. Where appropriate, these atoms include hydrogen (including all isotopes), hydroxy, oxo (=O), amino, or halo to satisfy the valence of the atoms. When the term "linker" is employed, unless stated otherwise or implicit from it use, it is intended to include direct attachment of the two groups without the introduction of any additional atoms.

The term "releasable" or "cleavable linker" means that the linker comprises a cleavable functionality—that is to say that the functionality or a covalent bond is readily cleaved into a first component and a second component by stimulation that breaks the bond. Such stimuli that can cleave a releasable bond include enzymes, UV light, heat, pH change, salt, and other components well known in the art.

The term "associated therewith" refers to any and all interactions whereby a first component becomes associated to a second component by, for example, its physical location, covalent bonding, ligand and receptor interactions, electrostatic interactions, magnetic interactions, hybridization, chelation, molecular sieve capturing, micelle or liposome formation, and the like. In a preferred embodiment, the term "associated therewith" utilizes either physical location, bonding or ligand receptor interactions. In some instances, the term "associated therewith" encompasses complementary functionalities where two functional groups when present are capable of becoming associated therewith.

The term "unique perturbation oligonucleotide," "perturbation oligonucleotide" or "PO" refers to an oligonucleotide that codes for the perturbation element on the perturbation bead wherein said PO is unique to other oligonucleotides used in the assay. In some embodiments, the unique perturbation oligonucleotide also codes for the unique label or set of labels on the perturbation bead In some embodiments, a label oligonucleotide (LO) can be attached to the PO to provide for a POL. That is to say that after forming the PO, a unique label oligonucleotide is then added at any stage of the assay to generate a POL group on the perturbation bead to identify the unique label or set of labels found on that bead.

Alternatively, during the synthesis of the perturbation element and the perturbation oligonucleotide in the split-pool reaction scheme, one or more steps of that reaction scheme can include the addition of a label to the perturbation bead and a corresponding oligonucleotide strand is added to the precursor oligonucleotide being formed on the bead. In such a case, the resulting PO will again code for both the perturbation compound and the unique label or set of labels Still further, only a sufficient number of labels and their corresponding oligonucleotide strands need be added during the synthesis of the perturbation element to uniquely define the label. So, assuming that in a 7-step split-pool reaction scheme using 10 reaction vessels in each step and that each perturbation bead can be uniquely labeled with 6 different labels, then, at a minimum, only 6 of the 7 steps need to add a label and a corresponding reaction step label oligonucleotide. That is to say that it is not necessary to label a perturbation bead at each reaction step when the number of reaction steps in the synthesis of the perturbation element exceeds the number of labels required to uniquely identify that bead. However, in practice, one can continue with labeling the perturbation bead at each reaction step even if such becomes unnecessary.

The term "static information" refers to changes in one or more cellular functions that have changed during the assay but collected after the assay is completed such as the expression of mRNA, upregulating or down regulating one or more cellular components that are captured by one or more capture beads such as chemokines, cytokines, hormones, enzymes, peptides, peptide fragments, and the like. Static information also includes perturbation components that are captured by the capture elements on the capture beads as well as perturbation components that can be analyzed directly in the lysed cellular milieu. For example, protein degradation components can be observed at the end of the assay but need not be captured to assess the perturbation components. In some embodiments, protein degradation components can be evaluated by immunofluorescent staining after the assay is completed if the perturbed and lysed cell is not from a stable cell line which contains innate fluorescence.

The term "dynamic information" refers to information regarding the cell as it occurs during the assay. Such dynamic information can include photo images of the cell undergoing perturbation including picture(s) or a video of the perturbed cell during a portion or all of the assay. Such images evidence changes in cellular functionality such as changes in cellular morphology, movement, size, shape, adhesion, division, induction of apoptosis, gene expression (e.g., expression of fluorescent/fluorescently labeled proteins), intracellular organization/structure (e.g., cytoskeletal organization/structure, organelle structure), extracellular expression, evidence of other cellular structural/behavioral changes, and the like. For example, such dynamic information may include optically detectable evidence of the presence of apoptotic markers or other markers, protein upregulation or downregulation that can be monitored live and/or in real time (e.g., fluorescent proteins, etc.), activation of T-cells thereby observing proliferation and change in their sizes, T-cells killing target cells, and the like. Such changes are deemed "live" or "real time" as they are observed as occurring during the assay and can be recorded via pictures, video recordation, three-dimensional analysis of the cell and the like.

As used herein, the term "or a precursor thereof" means that the distal end of the perturbation oligonucleotide either still bound to the bead or released from the bead and having a perturbation component bound to a first end, then the second end can be modified to provide for a second binding element. For example, if the distal end of the perturbation oligonucleotide has a poly-T binding element attached thereto, then, if the proximal end contains a known oligonucleotide leader sequence (not part of the code for the perturbation compound or label(s)), then that sequence can be used to attach a binding element thereto by hybridization. As such, the leader sequence would constitute "or a precursor thereof".

In all cases described above, at the completion of the split pool process, each bead will have a unique perturbation compound and a unique perturbation label compared to the other beads within a population of beads.

2. OVERVIEW

The perturbation beads and their corresponding methods disclosed herein utilize a population of beads each of which are uniquely labeled and each having a unique perturbation element attached thereto. In some embodiments, both the unique label and the unique perturbation element are coded by a releasable perturbation oligonucleotide bound to the perturbation bead. After release, the perturbation oligonucleotide is then attached to one or more perturbation components from a lysed cell. When these perturbation beads are used in an examination area of a mapped assay device, the transfer of the perturbation oligonucleotide and subsequent attachment to a perturbation component captured from the lysed cell allows a technician to correlate the sequence of nucleotides on the thus formed nucleic acid the code back to the label and, hence, the specific examination area from where the nucleic acid was retrieved. Knowing the examination area now allows the technician to review the images of that area during the assay and evaluate dynamic changes to the cellular functionality arising from release of the perturbation compound into the assay solution for contact with and subsequent perturbation of a cell. When this information is coupled with the nucleic acid sequencing information determined after the assay is otherwise complete, the technician can correlate these multiple functional changes to the cell thereby deriving a significantly deeper understanding of the impact the perturbation compound had on the cell during the assay.

Accordingly, the perturbation beads described herein are useful in ascertaining the change in functionality due to perturbations induced at the cellular level after the assay is complete but also allows for correlating the functional changes occurring during the assay. This allows collection of information both statically (at the end of the assay) as well as during the assay (dynamic changes") regarding the change in cellular functionality that occur during the assay.

In addition to static changes in cellular functionality, this disclosure provides for dynamic changes in functional that occur during the assay such as a picture(s) or a video of the perturbed cell. By collecting such images during a portion or all of the assay, a technician can assess the change in functionality evidenced by a change in morphology of that cell, evidence of the presence of apoptotic markers or other markers, protein upregulation or downregulation that can be monitored live and/or at the end of the assay, activation of T-cells thereby observing proliferation and change in their sizes, T-cells killing target cells, and the like. Coupling that information with static information provides for a more complete analysis of the impact of exposing the perturbation element(s) to the functionality of the cell.

The ability to correlate static and dynamic information means that one can couple multiple changes in cellular functionality into a more global analysis. As described herein, such is accomplished by including on the perturbation bead as disclosed herein.

It is understood that, in some embodiments, any perturbation can be used to perturb a cell. For example, the perturbation element can be a physical perturbation, e.g., stress, hypoxic conditions, different reaction condition such as a different pH, a different buffer, and/or a different salt, and/or a different concentration of buffer and/or salt, and/or a different length of time for the assay to be conducted, and the like. Still further, the perturbation element can be an antibody or a cell such an immune cell.

In some embodiments, the methods described herein can include the use of a capture bead that contains at least one binding element which captures oligonucleotides on the perturbation bead as well as the nucleic acids released upon lysing the cell in the examination area. In some embodiments, the capture bead optionally contains a unique set of labels but does not contain any oligonucleotides coding such labels on the capture bead. In another embodiment, the capture bead is devoid of any labels.

In some embodiments, the captured perturbation components bound to the capture bead with the perturbation oligonucleotide that codes for the unique label or set of labels on the perturbation bead provides for a complete set of information, including the perturbation element that perturbed the cell, the unique label on the perturbation bead, the nucleic acids recovered from the lysed cell. For example, the perturbation bead comprising a multiplicity of capture elements can utilize capture elements that have two capture components as described above in formula I:

(I)

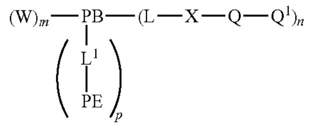

where both X and $Q^1$ are capture components and W, PB, L X, Q, $L^1$, PE, m, n, and p are as described above.

In some embodiments, the multiplicity of capture elements on the capture bead can have two binding components as described above in formula VII:

$(V)_r$-CB-$(L^4$-$X^1$-$Q^2)_b$ VII where $X^1$ and $Q^2$ can both be capture components.

Once releasing the releasable bond, $L^4$, is released from the capture bead and if the capture elements and the capture components are oligonucleotides or nucleic acids, then sequencing the resulting combination will provide the codes for the unique perturbation compound, the unique label or set of labels and the nucleic acids released from the lysed cell. The technician can then correlate this information back to the specific examination area using the map on the assay device. This then allows one to observe the dynamic changes in cellular functionality during the assay such as the changes in morphology and assign this to a particular capture bead. One can now combine the images of the examination area with all or some of this information using knowledge as to what examination area was used, what perturbation element was used in that examination area, what labeled bead was in that examination area, and what perturbation component was retrieved from that examination area by the capture bead to provide for substantial evidence of the static and dynamic changes in functionality that occurred during the assay.

Specifically, the methods and systems used herein include an assay device comprising a multiplicity of mapped examination areas such that each examination area is readily defined. Such mapping can include the X and Y coordinates for each examination area. Alternatively, each examination area in the device can be marked with a unique image or code. However, such is typically unnecessary when mapping the X and Y coordinates suffice. In those assay devices where the X and Y coordinates are ambiguous due, for example, to lack of uniformity of the examination areas to each other, marking each area will resolve the ambiguity. Still further, an indicia or mark can be applied to the assay device to orient the device along its proper X and Y axis. See, for example, FIGS. 1A and 1B.

In addition, the methods described herein permit the use of multiple perturbations in an examination area. For example, multiple perturbations can include a first perturbation designed to generate a second perturbation and the assay measures the impact of the second perturbation on a cell of interest. Such can be illustrated by using a perturbation compound (first perturbation) to contact and perturb a T-cell which then contacts a tumor cell to determine the impact of the perturbed T-cell on the tumor cell.

In some embodiments, when the capture element attached to the capture bead is an oligonucleotide ("capture oligonucleotide") configured to capture a nucleic acid from the perturbed and lysed cell, then the capture bead will also capture perturbation oligonucleotides including those that also code for the unique label on the perturbation bead.

When the perturbation oligonucleotide also codes for the unique label on the perturbation bead (POL), an optional linker or spacer can be used to separate that part of the oligonucleotide that codes for the structure of the perturbation element on the bead from the part that codes for the label. By combining these two components into a single oligonucleotide, a technician can rapidly correlate identity of the perturbation element with the label used to correlate that element to the examination area from which that element was found.

In some embodiments, there is provided a perturbation oligonucleotide that codes for the perturbation element and a unique label or set of labels associated with the perturbation bead and having a capture element attached thereto or can be modified to have a capture element attached thereto which said capture element is capable of capturing nucleic acids released by a lysed cell.

In some embodiments, there is provided a combination of a perturbation bead and a capture bead for use in a specific examination area of a mapped assay device. In some embodiments, the capture bead comprises one or more copies of a releasable capture element that captures the perturbation oligonucleotide released from the perturbation bead and/or perturbation components released from a lysed cell. Said combination is suitable for use in an assay that induces cellular perturbations and the corresponding perturbation components generated therefrom, said combination allows for a correlation between the nucleic acids to be sequenced to a specific is examination area in a mapped assay device suitable for use in an assay that induces cellular perturbations and the corresponding perturbation components generated therefrom.

In some embodiments, the capture bead is uniquely labeled, and, in other embodiments, the capture bead is not labeled. In some embodiments, the capture element is an oligonucleotide having from about 6 to about 2,000 repeating units of adenine, guanine, or cytosine. In some embodiments, the capture element is a ligand or receptor in a ligand-receptor axis. Such ligands include avidin (or streptavidin), biotin, antibodies, or antibody binding fragments, an enzyme, an enzyme binding domain, hormones and hormone receptors, and the like.

3. PERTURBATION ELEMENTS COMPRISING A PERTURBATION COMPOUND

In some embodiments, the perturbation element is a compound releasably bound to a perturbation bead. Such perturbation compounds are synthesized on the beads using conventional split-pool synthetic protocols well known in the art to generate a library of perturbation compounds. As per reaction scheme A below, which is provided for illustrative purposes only, a three-step synthesis for preparing a 1,000 member combinatorial library is depicted. Note that a four-step synthesis would provide for 10,000 possible compounds in the combinatorial library and a five-step synthesis would generate up to 100,000 compounds.

In step 1 of reaction scheme A, a plurality of beads (such as 1,000) is split into 10 vessels numbered 1-10 respectively (e.g., such that each vessel has approximately 100 beads). The beads comprise a cleavable linker for reacting with a component of interest to form the compounds that are to be made. In addition, there is an oligonucleotide site on the beads to which oligonucleotide strands can be added which, when finished will define the structure of the perturbation compound to be generated thereon or the reaction steps used to make that compound (perturbation oligonucleotide—as per above). In some embodiments, the oligonucleotide site on the beads can contain a poly-C (cytosine), a poly-G (guanine), or a poly-T (thymine) having up to 2,000 members. This oligonucleotide site is distal from the linker and allows for oligonucleotide strands described below to be attached thereto.

In some embodiments, if the releasable linker for the perturbation compound and the perturbation oligonucleotide are the same, then, when the perturbation compound is released from the bead, so too is the compound oligonucleotide. The releasable linker may be cleaved under any Reaction Scheme A

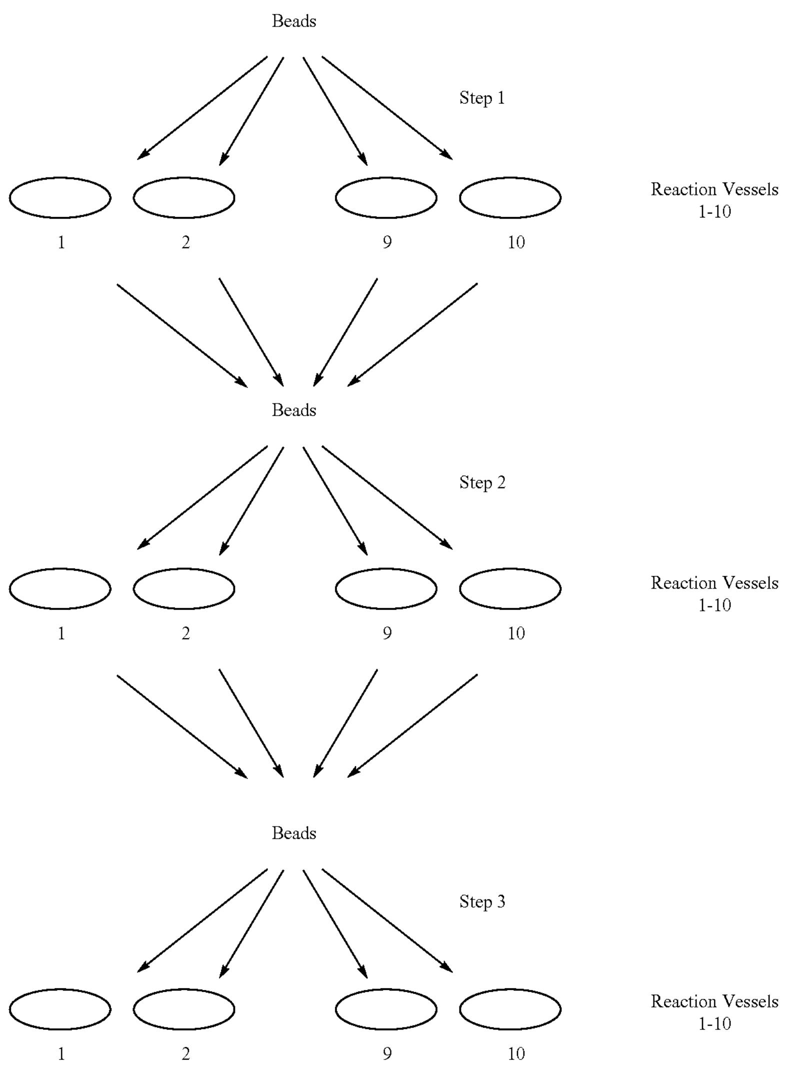

conventional means (e.g., UV light exposure, pH, etc., the use of uracil as a linker component which is cleaved by the U enzyme). In some embodiments, the releasable linker used at the perturbation oligonucleotide site is orthogonal to the releasable linker used for the perturbation compound made on the bead. In some embodiments, the linker used for the oligonucleotide binding site is non-releasable under normal conditions including that used to cleave the perturbation compound from the bead.

In some embodiments, a first unique label or labels is/are added to the perturbation bead in each reaction vessel by conventional methods such as click chemistry, amide bond formation, electrostatic binding or other suitable conjugation chemistries familiar to trained chemists. Also, or alternatively, a label and/or labels may be added as described in International patent application Serial No. PCT/US24/23594, entitled "Molecular Library Encoding System and Methods", filed Apr. 3, 2021, and/or International patent application Serial No. PCT/US24/23594, entitled "Cell Transfer Component for Multi-Well Assay Device", filed Apr. 8, 2024, which applications, and applications from which they claim the benefit of priority, are incorporated by reference herein in their entirety.

Alternatively, if the perturbation beads are provided as subsets, where each subset comprises a uniquely labeled bead distinct from beads in other subsets, then a single unique subset can be added to each vessel in the first step of the synthesis using approximately the same number of beads in each reaction vessel. This results in 10 reaction vessels which contain a population of beads where the beads in a given vessel all have the same unique label as compared to the labels on beads in the other vessels. In some embodiments, oligonucleotide coding the first step of the reaction in a given vessel and which is unique to that vessel will also code for the unique label used in that vessel.

In some embodiments, not all of the reaction steps in a split-pool synthesis need to be labeled. For example, in an 8-step synthetic process, it is possible for a unique set of labels to be added to the perturbation bead by the sixth step. In such a case, use of additional labels in the $7^{th}$ and $8^{th}$ steps becomes unnecessary and not conducted. So, this embodiment, the addition of labels in the split-pool synthesis is terminated once a unique label or set of labels is added to the perturbation bead.

Generally, a unique oligonucleotide strand for each reaction vessel can be introduced either before, during or after each reaction step and attached to the precursor strands to memorialize the reaction performed. During this step, a label or set of labels is added each of the beads in a given vessel and an oligonucleotide strand is attached to the precursor strand of oligonucleotide formed therein, which codes for the label and reaction conducted in or to be conducted in that vessel. Alternatively, as noted above, a separate oligonucleotide strand can be used to separately identify the label or labels added. In this case, it makes no difference if the first unique oligonucleotide strand coding for the label is added before or after the oligonucleotide coding for the reaction step.

Further in Reaction Scheme A, a first component of the perturbation compound to be synthesized can be added to the bead using chemistry that provides for very high yields (e.g., Click chemistry). The reactions can be run under conventional conditions that are maintained until the reactions are deemed complete. At this point, the beads comprise 10 different building blocks (e.g., beads in vessel 1 comprise a first building block in vessel 1, beads in vessel 2 comprise a second building block in vessel 2, and so on until the beads in vessel 10 comprise a tenth building block in vessel 10).

In step 2, all of the beads from each of the reaction vessels are typically washed and then pooled and mixed (e.g., shaken, stirred, etc.) to insure homogeneity. The beads are then split into a second set of reaction vessels in the manner described above (e.g., resulting in an approximately equal number of beads in each vessel). Each reaction vessel will receive a portion of the beads previously subjected to reactions in vessels 1-10. As such, each reaction vessel will receive beads comprising each of the 10 building blocks (e.g., beads comprising the first building block, beads comprising the second building block, etc.) The reaction vessels for step 1 can be used for step 2 (e.g., after washing vessels and/or otherwise removing any reagents remaining from the prior step). The unique reactions to be conducted and the unique label to be added to the perturbation beads in each vessel are memorialized by addition of another strand of an oligonucleotide unique to each reaction vessel which codes for the structural component added to the bead as well as the label. Alternatively, a separate unique oligonucleotide strand coding for the label can be added to the oligonucleotide strand coding for the reaction to each of the beads in a given vessel. The oligonucleotide strand(s) is/are attached to the prior oligonucleotide strand to from a single extended strand. The beads are then pooled and mixed as described above. At this point, the beads comprise up to 100 different building blocks. Further additional steps can be conducted in a manner similar to Step 2 and repeated as many times as desired to form the combinatorial library.

In step 3 (e.g., the final synthesis step), the beads are once again split and added to different reaction vessels in the manner described above. As above, the reaction in step 3 results in the generation of 1,000 compounds on the beads preferably with different components/reactions being used in each vessel in each step. The generated library of compounds on the beads can be tested for activity with a cell, for example, in an assay where a single bead and a small number of cells (e.g., up to 250 cells, up to 50 cells, around 20-30 cells, down to a single cell) are combined.

In some embodiments, when the addition of labels to the perturbation bead is complete such that each bead in a population of beads has a unique label or set of labels associated therewith, then the final step can either utilize an oligonucleotide strand to identify the component added to the compound to be synthesized thereby identifying the compound or the reaction steps used as described above or, unlike steps 1-2, described above, no oligonucleotide is added to memorialize the reaction in step 3. Rather, the beads from each vessel are washed and optionally dried and then are placed into an isolated location on the assay device (i.e., beads from each vessel are transferred to separate locations on a single assay device or into separate assay devices, wherein the separate locations or separate assay devices each contain examination areas, such as wells or droplets, for conducting the assay). Alternatively, the beads from each vessel are placed in separate assay devices marked with the reaction vessel from which they were retrieved. This allows the technician to immediately identify the last step of the reaction used for those examination areas that evidence interesting results.

Perturbation beads typically contain an excess of reactive sites over that which will be populated by the synthesis of the perturbation element and the formation of the perturbation oligonucleotide. This excess allows for the formation of a further oligonucleotide on the beads that codes only for the label or set of labels that are associated with that bead. This allows for the generation of a beads depicted in Formula IX and/or X above.

4. OTHER PERTURBATION ELEMENTS

Other perturbing elements that are useful in the assays described herein include agents such as antibodies, immune cells, synthetically engineered cells, siRNA, viruses, bacteria, fungi, a change in one or more the conditions of the assay such but not limited to buffers, salts, pH, temperature, nutrients, oxygen levels, oxidizing agents, physical stress, and the like. Each of these can be used alone or in combination with one or more of such agents including a perturbation compound.

As to immune cells, their addition to an examination area allows for the evaluation of whether an immune cell will perturb a cell such a tumor cell in a therapeutic manner. In addition, the examination area also can contain a perturbation compound to evaluate whether that compound will perturb an immune cell which previously was either non-responsive or marginally responsive in a manner rendering the immune cell therapeutic to the tumor cell. Still further, the immune cell can be used alone or with a perturbation compound added to assess whether such attenuates or enhances the activity of that cell.

As to antibodies, the addition of a weakly reactive antibody into an examination area containing a tumor cell allows for the addition of a perturbation compound that perturbs the tumor cell. One can then evaluate whether the perturbation induced in the tumor cell enhances the therapeutic activity of the antibody.

As to engineered cells, these may comprise cells engineered to secret or express membrane associated agents capable of interacting with the test cells in the examination area. In some embodiments, the engineered cells may be engineered to secrete synthetic proteins, cytokines or antibodies. In some embodiments, the engineered cells may by engineered to produce unique small molecules or metabolites. Engineered cells are the foundation of biotechnology and the various methods are well known to technicians engaged in the art of biotechnology and/or synthetic biology.

As to other perturbation agents, the use of conditions to perturb a cell provides valuable information as to whether the perturbation is beneficial or detrimental to the cell. Where conditions are detrimental, therapeutic agents which induce a similar perturbation to a diseased cell are appropriate candidates for inducing similar changes in vivo.

As per the above, combinations of perturbing agents can be used to ascertain the perturbation impact of combination as compared to the separate perturbating agents when used alone.

The salient feature of the perturbation beads is their ability to self-identify the bead and its location in an examination area of an assay device. The self-identification aspect is due to the fact that the perturbation bead is identified by both a unique label or set of labels which is coded into the perturbation oligonucleotide thereby allowing sequence of that oligonucleotide, once freed from the perturbation bead, to self-identify the unique label or set of labels on that bead. This, in turn, allows the unique label or set of labels to be correlated to the examination area by reference to the registry.

5. CAPTURE BEADS

Capture beads, as described herein, comprise a multiplicity of capture elements which are used to capture perturbation oligonucleotides as also described herein as well as perturbation components generated by a perturbed cell during the assay. In some embodiments, the perturbation oligonucleotide does not code for the unique label on the perturbation bead, but rather a separate label oligonucleotide is used. If the label oligonucleotide is released from the perturbation bead without attaching to the perturbation oligonucleotide, then the capture element will also capture label oligonucleotide. The capturing process is preferably conducted in a manner such that each captured component is provided in a linear fashion such that sequencing will provide the technician with information as to the unique perturbation element used, the unique label on the perturbation bead, and the perturbation components released from the lysed cell. In such an embodiment, when the label oligonucleotide having one or 2 capture elements is released, it can be added to a capture element on perturbation oligonucleotide on the capture bead, or the perturbation oligonucleotide having one or two capture elements can be added to a second capture element on label oligonucleotide where the other capture element is hybridized to the complementary capture element on the capture bead. Or the capture bead can have two capture elements which can separately capture both the perturbation oligonucleotide and the label oligonucleotide. As is apparent, either or both of the label oligonucleotide and/or the perturbation oligonucleotide can have a second capture element. This allows the technician to associate the perturbation components to the perturbation element and the perturbation bead. In turn, using the register of each perturbation bead used in each examination area, the technician can now determine the cell that produced the perturbation components in response to contact with the perturbation bead.

For illustrative purposes only, when the perturbation oligonucleotide codes for the perturbation element as well as for the unique label on a given perturbation bead and when the perturbation element is released from the bead together with perturbation oligonucleotide by using a common releasable linker, then the capture element on the capture bead will capture the perturbation oligonucleotide by employing a complementary group that attaches to a functional group on the perturbation oligonucleotide. The following non-limiting example illustrate such an embodiment:

A capture bead has bound thereto through a releasable linker a biotin group. The perturbation oligonucleotide employs at its proximal end an avidin group releasably attached by a linker to the perturbation bead. The perturbation oligonucleotide also includes a poly-T group at and/or attached to its distal end. The perturbation bead employs the same releasable linker for the perturbation oligonucleotide as for the perturbation element. The releasable linker used on the capture bead can be the same or different from that used on the perturbation bead. If different, the different linker on the capture bead is preferably released by orthogonal means to that on the perturbation bead. In addition, the perturbation oligonucleotide codes for both the perturbation element and the unique label or set of labels on the perturbation bead. This embodiment is illustrated in Reaction Scheme B below:

REACTION SCHEME B

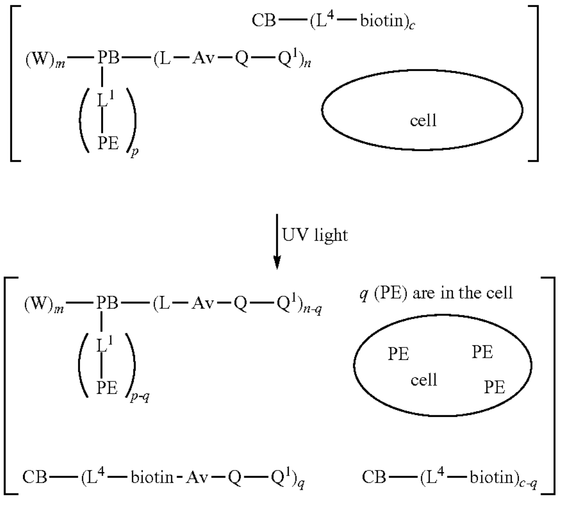

In this reaction scheme, W, PB, PE, L, $L^1$, Q, $Q^1$, m, n, and p are as defined above, AV refers to avidin (or streptavidin), CB refers to the capture bead, and c refers to the number of biotin capture elements on the capture bead maintained there by a releasable group $L^4$ which is released in a manner orthogonal to L and $L^1$, q refers to the number of groups released by UV light cleaving L and $L^1$.

Each examination area contains a perturbation bead, a capture bead and a cell, which are maintained under standard assay conditions as indicated by the brackets. Standard assay conditions may comprise media, gas components, temperature, and any growth factors and adhesion factors that may be required for viability and health of the cell. The assay device contains a multiplicity of additional examination areas each containing the above components albeit with different perturbation elements and perturbation oligonucleotides in a standard assay solution. The examination area is exposed to UV light for a sufficient period of time to cleave a portion of the releasable bonds attaching both the perturbation element and the perturbation oligonucleotide to the perturbation bead. In this case, when L and $L^1$ are the same, reaction scheme B assumes that an equal number of q groups are freed.

After exposure of UV light to the examination area, the products as shown include an unreacted portion of the starting materials indicated by reducing their numbers by q. In addition, the number of PE released is q which for the sake of illustration is shown as all being in the cell to initiate perturbation. In addition, an equal number of Av-Q-$Q^1$ groups released from the perturbation bead have become bound to the capture element on the capture bead. As is apparent, this is an idealistic illustration as not all of the Av-Q-$Q^1$ will bind to the capture element on the capture bead, nor will all of the PE be absorbed by the cell.

The released perturbation element (PE) interacts with the cell with the cellular surface or in the intracellular domain thereby inducing a response (perturbation) from the cell. This portion of the assay is continued as deemed sufficient and images of individual examination areas are taken periodically or continuously.

Afterwards, if the perturbation causes morphological or other functional changes in the cell during the assay, such changes can include undulations, protrusions, as well as the presentation of new and/or loss of existing cell surface markers, the presence of apoptotic changes, as well as other changes in the cell. Such changes can be captured or recorded by imaging, for example. When the assay is completed, the cell is lysed by conventional conditions such as exposure to a detergent solution. This is illustrated in Reaction Scheme C as follows:

Reaction Scheme C

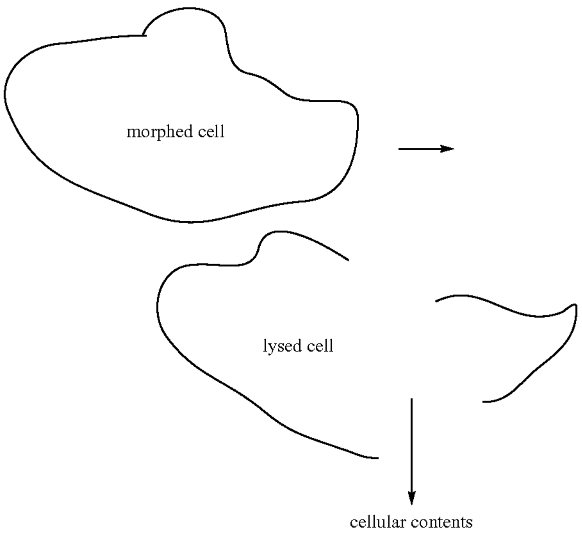

Lysing of the perturbed cell is conducted in the presence of CB-($L^2$-Av-Q-$Q^1$)$_q$ where for each of the q $L^2$-Av-Q-$Q^1$ groups, $Q^1$ can be the same or a different binding element such that $Q^1$ can capture nucleic acids such as mRNA when $Q^1$ is poly-T, and when $Q^1$ is a complementary functionality other cellular contents such as cytokines, chemokines, enzymes, etc., then $Q^1$ will capture these perturbation components.

In some embodiments, the capture elements on the capture beads and the corresponding complementary functionality on the perturbation oligonucleotides and the nucleic acids to be captured are all attached to each other to form a continuous oligonucleotide attached at one end to a nucleic acid. In such an embodiment, when so released from the capture bead, the solution phase product can be sequenced to provide the technician with information including the nucleic acid generated by the perturbed cell, the structure of the perturbing compound, and the code for the set of labels on the perturbation bead. This allows the technician to reference the register of mapped examination areas and identify the address of the examination area from where the perturbation was found. Coupling of the information regarding the examination area with the images of that area allows the technician to now associate the dynamic functional changes recorded during the assay with the static functional changes found in the nucleic acids.

In some embodiments, the capture element comprises a poly-C or poly-G group releasably attached to the capture bead. In this embodiment, the perturbation oligonucleotide will have a complementary poly-G or poly-C group instead of the avidin/streptavidin group but will retain a poly-T group at the opposite end. When the perturbation oligonucleotide is released from the perturbation bead, the complementary groups will hybridize for attachment of the perturbation oligonucleotide to the capture bead. In this embodiment, the remainder of the process is similar to that described above.

In addition to nucleic acids which are released from the lysed cell other perturbation components that can be retrieved include, by way of example, cytokines, chemokines, enzymes, proteins, hormones, and the like. Such a diverse selection of perturbation components not only allows the technician to assess the changes generated by the perturbation as compared to an unperturbed cell but also to assess whether such changes are beneficial or not. In total, a technician can provide a more thorough evaluation of the changes in functionality of the cell due to the perturbation by assessing as many components as possible.

As above, when the perturbation component is mRNA, it can be captured by poly-T. As to cytokines and chemokines, a receptor specific for these can be attached to the capture bead. Likewise, enzymes can be captured by a substrate to which they act upon, and the like. Suffice it to note that the extent of targets to be captured by the capture bead is limited only by the recognition of a binding element specific for the target. In some embodiments, a binding element can be created for a particular perturbation component. For example, monoclonal antibodies can be generated by conventional means to bind to a specific perturbation component generated during the assay.

In some embodiments, multiple capture beads can be used in a single examination area. Each capture bead is directed to capturing different perturbation elements from the lysed cell. For illustrative purposes only, a first capture bead has bound thereto multiple copies of the same capturing element for mRNA. A second capture bead has bound thereto multiple copies of the same capturing element for a specific cytokine. Additional capture beads can be used to bind to other perturbation components.

As to optically detectible labels, W, such can include one or more colors, induced colors, lettering, numbering, images, insignia, barcodes, quantum dots, QR codes and the like.

In some embodiments, X is a capture element as defined herein and $Q^1$ is a capture element which has captured, for example, a perturbation oligonucleotide while retaining a further capture element at the terminal end of the perturbation oligonucleotide.

The composition of perturbation beads and capture beads for use herein is not critical as long as the perturbation beads can be labeled and modified as herein described. In some embodiments, either or both of the perturbation and capture beads can be polydimethylsiloxane (PDMS), polystyrene, glass, polypropylene, cyclic-olefin polymers, cyclic-olefin copolymer, agarose, gelatin, hydrogel, paramagnetic, ceramic, plastic, methylstyrene, acrylic polymer, titanium, latex, Sepharose, cellulose, nylon, silicone, and any combination of the above. The particular material used for the capture bead is conditioned only on it being made of material that is inert to the assay to be conduct including the solvent and reagents used.

In some embodiments, the size of each bead corresponds to a percentage of the size of the examination area where larger examination areas tolerate larger capture beads. In general, the size of each bead ranges from about 5 percent to about 50 percent of the size of the examination area. In absolute size, the capture bead is preferably from about 10 microns to about 250 micron along its longest axis and, more preferably from about 20 microns to about 200 microns along its longest axis, and even more preferably from about 30 to about 180 microns along its longest axis.

In some embodiments, the capture bead is added after assay completion where each of the capture elements as well as is releasable bound to the capture bead. By adding the capture bead after assay completion, any cleavable bonds used with the capture components can be the same as that used during the assay. Once the capture bead is recovered, the captured components bound to the bead can be released and then determined by conventional means.

6. REAL TIME ANALYSIS

As above, this disclosure provides the technician with the ability to associate the perturbation component(s) generated by the perturbed cell to a specific perturbation bead and then back to the examination area where the perturbed cell was located by reference to the map on the mapped assay device. In turn, generating a record of each cell in each examination area that encompasses the assay period, one can access that record and assess the cellular changes that can be visibly observed as a result of the perturbation.

Such cellular changes include changes in morphology, movement, size, shape, adhesion, division, induction of apoptosis, gene expression (e.g., expression of fluorescent/fluorescently labeled proteins), intracellular organization/structure (e.g., cytoskeletal organization/structure, organelle structure), extracellular expression, evidence of other cellular structural/behavioral changes, and the like. Such changes are deemed "real time" as they are observed as occurring during the assay and can be recorded via pictures, video recordation, three-dimensional analysis of the cell and the like.

The technician can then combine the real time changes in functionality with the static changes and provide a substantially improved overview of the cellular changes in functionality.

7. SYSTEMS

In some embodiments, there is provided a system for providing static and dynamic information regarding the impact of a perturbation element on a cell in an assay said system comprises:

a) a mapped assay device comprising multiple examination areas that are individually identifiable;
b) a perturbation bead comprising:
  a multiplicity of a perturbation element releasably bound thereto which element is unique to other perturbation beads to be used in the assay device;
  a label or set of labels that uniquely identify that bead from other beads to be used in an assay; and
  a multiplicity of a perturbation oligonucleotide that codes for the perturbation element as well as the label or set of labels on the perturbation bead;
c) a capture bead as described herein;
d) a cell; and
e) a register that correlates each perturbation bead to a specific examination area.

The systems described herein can further comprise one or more additional capture beads, one or more additional cells, a combination of perturbation elements that act cooperatively (a first perturbation element that perturbs a second perturbation element that then perturbs a cell of interest). In some embodiments, sequencing of oligonucleotides bound to the capture bead can be done on the bead itself. In another embodiment, sequencing is done after releasing the oligonucleotides by cleaving the releasable bonds.

8. ASSAY PROTOCOLS

The assays described herein are conducted in a mapped assay device having a multiplicity of examination areas. For illustrative purposes only, the assays described herein employ a perturbation bead having a unique label or set of labels associated therewith and multiple copies of the same perturbation element releasably bound thereto and a perturbation oligonucleotide that memorializes all or part of the reaction steps used to make such elements, and further codes for the unique label or set of labels. Again, for illustrative purposes only, the perturbation element is a compound, and the perturbation oligonucleotide has attached thereto a poly-T component that permits its capturing by a poly-A capturing element on the capture bead.

Each examination area in the assay device includes a perturbation bead as described above, at least one cell (e.g., up to 250 cells, up to 50 cells, around 20-30 cells, down to a single cell) to be perturbed, a capture bead as described herein including multiple copies of a capture element, and an aqueous solution suitable for conducting the assay. For illustrative purposes only, in this embodiment, the captured oligonucleotide and the capture element are attached to each other and to the capture bead in a manner where each attachment is optionally through a linker.

The identity of each perturbation bead in each examination area as well as the capture bead itself is memorialized or recorded by identifying the label on each perturbation bead, and optionally the capture bead, and corresponding to an examination area that is mapped within the assay device. This provides a 1:1 correlation between each examination area and each perturbation bead/capture bead maintained therein merely by referencing the unique label or set of labels found on the perturbation bead to the mapped examination area.

The assay is initiated by releasing at least a portion of the perturbation element (compound) bound to the perturbation bead into the aqueous solution in a sufficient amount to perturb the cell. In some embodiments, the releasing mechanism (e.g., UV light) will also release the perturbation oligonucleotide from the perturbation bead as well as any releasable bonds on the capture bead that are responsive to release using the same releasing mechanism. In addition, in this embodiment, the released perturbation oligonucleotide will be captured by the capturing element which associates with the complementary functionality of the perturbation oligonucleotide. In some embodiments, the complementary functionality on the perturbation oligonucleotide is Poly-C, Poly-G, Poly-T, avidin, streptavidin or biotin. In some embodiments, the perturbation oligonucleotide comprises a second complementary functionality that is the same or orthogonal to the first or which can be introduced onto the perturbation oligonucleotide after it is bound to the capture element. The assay is then conducted for a sufficient period of time to induce one or more cellular perturbation(s). In some embodiments, images of the cellular response to the perturbation can be made. Upon completion of the assay, the cell is lysed to release cellular contents.

Upon release, the mRNA of the released cellular contents is captured by the poly-T capturing elements on perturbation oligonucleotide bound to the capture bead. Other cellular contents can be captured by capture elements on the capture bead that are complementary to the target to be captured. In some embodiments, the capture bead is isolated from the examination area, washed, and prepared for sequencing. In some embodiments, each of the capture beads in the multiplicity of examination areas used are pooled, then the perturbation oligonucleotide and the attached nucleic acids are released from the beads by cleaving the releasable bond between the capture bead and the capture element. Sequencing of each of the perturbation oligonucleotide coding for the perturbation element and the unique labels on the perturbation bead will self-identify the particular perturbation bead from which the perturbation oligonucleotide was attached and by reference to the register, the examination area where that bead was placed (the "address") as well as the nucleic acid expression generated or altered by the perturbation. In some embodiments, the imaging captured from that examination area is combined with the information garnered by sequencing to provide a robust detail of both the dynamic functionality changes in the cell as well as the static changes that the changes in dynamic functionality induced. This provides the technician with a substantially more sophistic analysis of the change in cellular functionality that otherwise could be made.

In some embodiments, images are created or memorialized including the digital photograph(s) or digital video recording. The digital aspects of such records allow for rapid assessment of colored labels used to uniquely identify a particular capture bead. In some embodiments, the differential intensity of a single color can be used to generate a multiplicity of labels that are distinguishable. For example, digital photography codes the pixels for color and intensity which is readily distinguishable from the same color at a different intensity due to the pixel count.

As noted previously, the capture bead can be added to the examination area prior to, during, or after the assay completion. However, addition of the capture bead into the examination area before the start of the assay is preferred as it makes recordation of the examination area address to the particular perturbation bead easier if for no other reason that assay debris can be avoided when recordation is done.

9. EXAMPLES

The following examples are provided to illustrate the use of a perturbation bead as described herein. In this example, the following terms used therein have the following meanings:

bp=base pairs
poly-A=poly adenine
poly-T=poly thymine
poly-G=poly guanine
poly-C=poly cytosine
mRNA=messenger RNA
UV=ultraviolet

Example 1—Assay Device

Figure 1B:
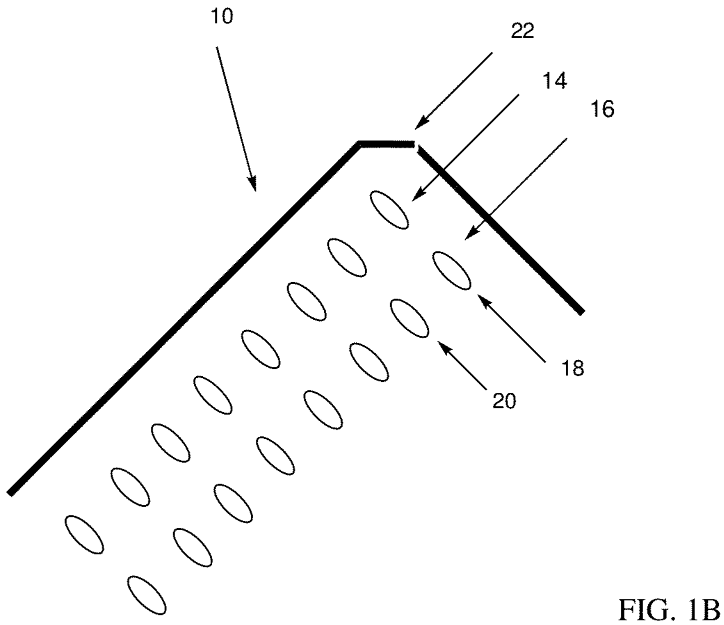

A mapped assay device is employed which comprises a multiplicity of examination areas (e.g., picowells). Each picowell is aligned in rows and columns such that the number of columns is longer than the number of rows. To orient the assay device, a mark, emblem, or other distinguishing feature can be added to one corner of the device to indicate an "up" position and/or standard orientation. FIG. 1A illustrates the arrangement of examination areas in a portion of a mapped assay device. Specifically, mapped assay device 10 has a mark, 12 in a corner of the device 10 that directs the user to reference that corner as the upper left corner of device 10, for example. Any mark, indentation or other feature can be used provided that it orients the device such that individual examination areas can be identified by columns 14, 16 and rows 18, 20. FIG. 1B shows an alternative means of orienting the device 10, wherein an indentation 22 differentiates one corner of the assay device 10 from the others. In any case, a mapped assay device is provided where each examination area is identifiable by a column (e.g., 14, 16) and row (e.g., 20, 18). Any other distribution of examination areas may be used, as long as they can be unambiguously mapped.

Example 2—a Library of Perturbation Beads

Step 1. A population of approximately 100,000 beads each having multiple copies of a same oligonucleotide binding site and multiple copies of a compound synthesis site bound thereto are commercially available from Rapp Polymere GmbH, Ernst-Simon-Strasse 9, 72072 Tuebingen, Germany. In some embodiments, the beads comprise a releasable functional group proximal to the bead and a first binding element such as a poly-C, poly-A, or poly-G oligonucleotide binding site distal to the releasable group relative to the bead. The beads are divided in approximately equal number into 10 different reaction vessels. A unique first step of compound synthesis is conducted in each vessel such that each vessel generates a distinct building block different from the other building blocks generated in the other vessels. Either before, during or after reaction completion, a first oligonucleotide strand that is unique for each reaction vessel is added to the oligonucleotide binding site such that all of the beads in the same reaction vessel will have the same first oligonucleotide strand which is different from the oligonucleotide strand found in the other vessels. In addition, either before or after the first reaction step is completed, the bead has a label or set of labels associated thereto and the first oligonucleotide strand also codes for that label or set of labels. The addition of a first label is conducted as per below. After completion of the first step of the compound synthesis the beads are washed and then combined and homogenized.

Step 2. The procedure of Step 1 is repeated but using a unique second building block for compound synthesis in each of the 10 reaction vessels as well a unique second oligonucleotide strand for each reaction vessel and a second label or set of labels. Again, the unique second oligonucleotide can also code for the second label or set of labels added to the bead. After completion of this step of the compound synthesis the beads are washed and then combined and homogenized.

Steps 3-5. The procedure of Step 2 is repeated but using a unique third, fourth, and fifth building block for compound synthesis as well as a unique third, fourth and fifth perturbation oligonucleotide strand coding for each building block and for each label or set of labels. In the last step of adding an oligonucleotide strand, a second binding element such as poly-T is included in the distal end of the strand.

After step 5, there are approximately 100,000 different compounds made on the approximate 100,000 different beads. Each of these beads is now uniquely labeled with a set of labels provided that the theoretical likelihood of duplication is no more than 1 in 10,000 beads and, in some embodiments where a further reaction step is included, no more than about 1 in 100,000 beads.

A single perturbation bead is then added to a single examination area in the assay device. Such a perturbation bead can be illustrated as shown in Formulae I' or I:

(I')

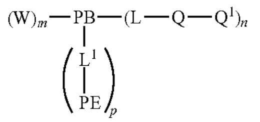

or (I)

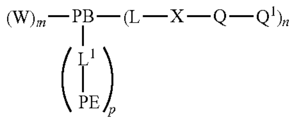

where:

- W is an optically detectable label or a set of optically detectable labels that uniquely identify the perturbation bead;
- PB is a perturbation bead;
- PE is a perturbation element;
- L is a releasable linker;
- $L^1$ is a releasable linker which may be the same or different from L, and when different, L and $L^1$ may be cleaved with the same stimulus or with different stimuli;
- Q is a perturbation oligonucleotide that codes for at least a portion of the perturbation element and the unique label or set of labels;
- $Q^1$ is a binding element;
- X is a bond (formula I) or a binding element (formula IA);
- m is an integer from 1 to about 100 (or more, depending on the type of label and size of bead, for example);
- n represents the multiplicity of such (L-Q-$Q^1$) or (L-X-Q-$Q^1$) groups bound to the perturbation bead; and
- p represents the multiplicity of such (PE) groups bound to the perturbation bead.

Example 3—Labeling Perturbation Elements

The process for adding a label to the perturbation bead at each step of the split-pool synthesis is conducted in situ in the reaction vessel by click chemistry, for example.

Example 4 Capture/Perturbation Bead

Each capture or perturbation bead can be made from the starting materials described above and otherwise herein. Each of the perturbation beads (and optionally the capture bead) have bound thereto a label or set of labels comprising oligonucleotides, fluorescent particles, micro-components, such as semiconductor microchips/micropucks, etc., or combinations thereof that uniquely define the perturbation bead. In addition, a binding element is attached to the capture bead using, e.g., for example, a poly-C group for binding to a poly-G group on the perturbation oligonucleotide. Other binding elements can be used as described herein. In some embodiments, a perturbation oligonucleotide is first attached to the perturbation bead using methods well known in the art such as those in Examples 1 and 2. As above, each perturbation oligonucleotide is unique to the perturbation bead in a given examination area.

In some embodiments, a perturbation bead having a poly-G capture element can be hybridized with a poly-C group on the perturbation oligonucleotide.

Perturbation and/or capture beads may be labeled with a label or set of labels that uniquely identify the bead by any means discussed or referenced herein, including the following examples. FIGS. 2A-2D illustrate different optically detectible labels placed on a perturbation bead that uniquely distinguish that bead from other perturbation beads. Specifically, a unique combination of fluorescent dyes and/or their intensity of signal can be covalently attached to a perturbation bead such that the fluorescent signals generated can be associated specifically with that bead. In FIG. 2A, the first Y can be at one-third of the intensity of the second Y thereby distinguish a first Y from a second Y A large number of quantum dots are commercially available from ThermoFisher, Tempe, Arizona, USA, for example, and can be used for this purpose. The number of such dots required per capture bead is a function of the number of examination areas to be used in the assay device. For example, ten uniquely identifiable quantum dots can provide for over 3,000,000 unique combinations. In FIGS. 2A-2D, B stands for blue; G stands for green, O stands for orange, R stands for red, and Y stands for yellow. In each case, the combination of colors using only these 5 colors provides for 120 unique combinations which is greatly expanded by adding just another 5 colors as above.

Figure 3:
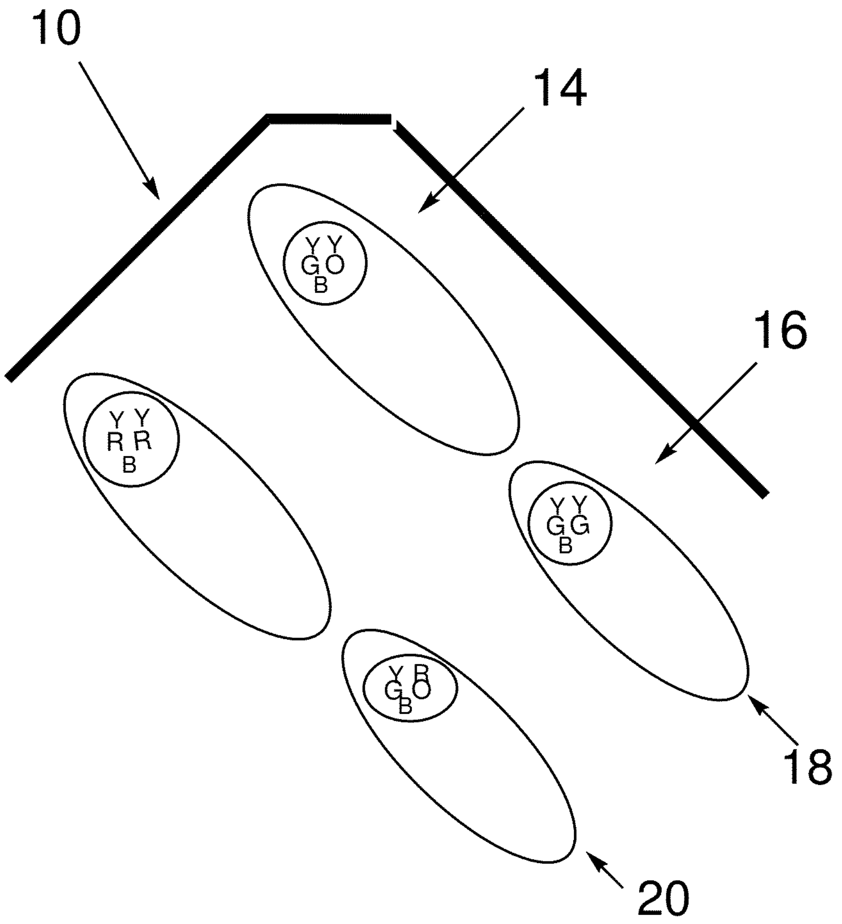
FIG. 3 illustrates the perturbation beads of FIGS. 2A-2D in a subset of examination areas depicted in FIG. 1B.

FIG. 3 illustrates placement of the labeled beads of FIGS. 2A-2D into separate examination areas as of an assay device 10 as illustrated in FIG. 1B.

Figure 4:
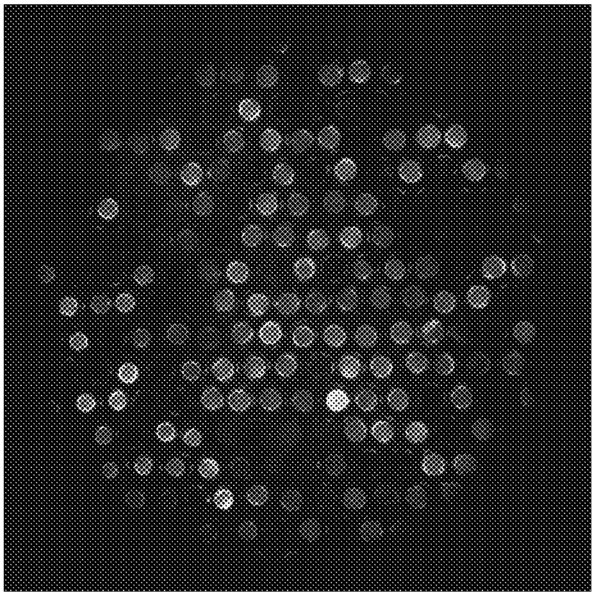
FIG. 4 illustrates a mixed bead population having beads of different colors and different color intensity for the same colors.

Also, or alternatively, perturbation beads and/or capture beads can be impregnated with or bound (e.g., covalently) to dyes such that each perturbation bead and/or capture bead has a distinguishable color or fluorescent generated color that acts as a label and differentiates it from other perturbation beads. FIG. 4 illustrates an assay device with one bead per well, wherein each well contains an optically distinguishable beads with different color and intensities. In short, the beads are TENTAGEL™ beads that were formed by suspending one of:

1. 14 mg S30902 TENTAGEL™ resin, 10 ul QD600-WS quantum dot
2. 11 mg M30202 resin, 10 ul QD540-WS quantum dot, or
3. 11 mg M30352 resin, 10 ul QD680-WS quantum dot in 400 μL water for 20 minutes for equilibration in 1.5 mL Eppendorf tubes (quantum dots from NanoOptical Materials—CuInZnS/ZnS core/shell Quantum Dots with central emission peaks of 600 nm, 540 nm, and 680 nm, respectively). 4 mg 1-ethyl-3-(3-dimethylaminopropyl)carbodiimide (EDC −) in 100 μL water was then added to each tube and allowed to react at room temperature for 16 hours with sporadic agitation. This resulted in a TENTAGEL™ beads embedded with QDs emitting different colors and/or at different intensities such that each bead is uniquely distinguishable from the others by color and/or intensity.

Digital cameras record color and intensity of the color by pixels. Accordingly, two dots of the same color but of different intensities can be readily distinguished by the pixels used to correlate differential intensities. This is readily done by computer analysis of the pixels.

Also, or alternatively, perturbation beads and/or capture beads can be labeled with one or more micro-components that either have a detectable code thereon (e.g., FIG. 5A-B) or that form and/or constitute a detectable code (e.g., FIG. 5D) that uniquely labels the corresponding beads.

Figure 5A:
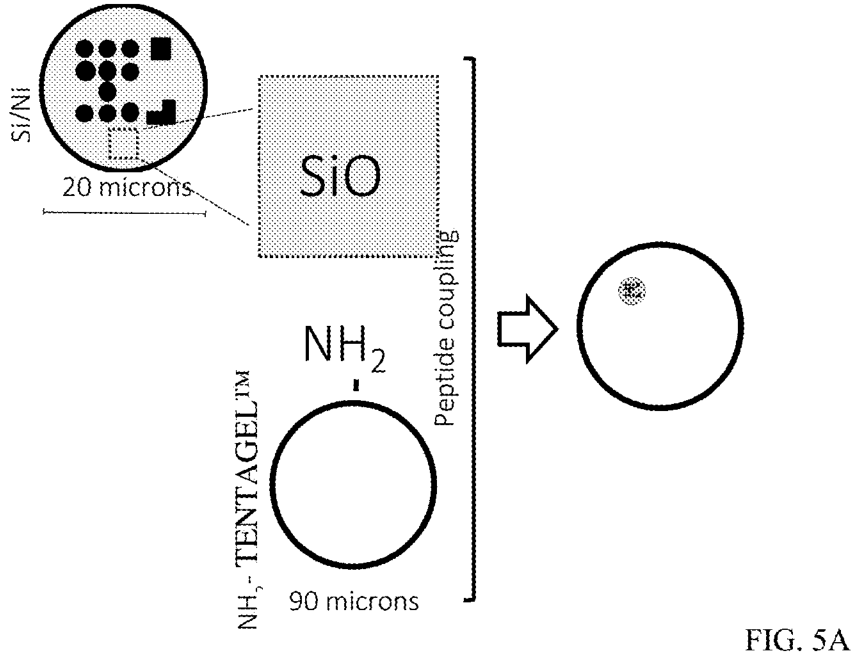
FIGS. 5A-5D show examples of labeling and labeled beads with micro components.
Figure 5B:
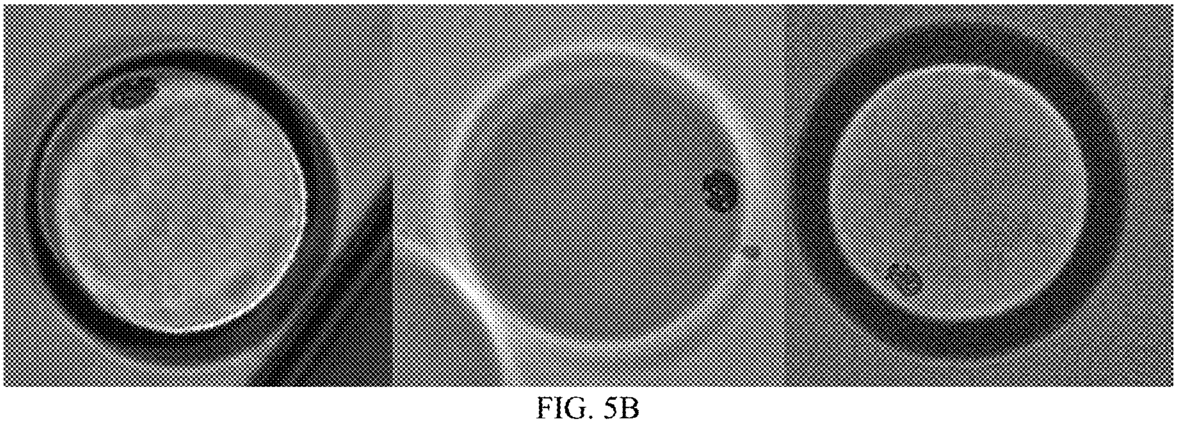

FIG. 5A shows an schematic for labeling a bead (in this example, a 90 micron TENTAGEL™ microbead—could be used as a perturbation or capture bead) with a micro-component (in this example, a silicon micropuck) having a visibly distinguishable code fabricated thereon. A layer of silicon oxide was deposited on silicon micropucks under ambient conditions, such that acidic silanols (SiOH) were formed on the surface of the micropucks. Silanols reacted readily with amine groups on the TENTAGEL™ beads (e.g., 90 micron TENTAGEL™ beads) resulting in stable electrostatic interactions that are stable under many solvents and reaction conditions. FIG. 5B shows three beads having encoded silicon micropucks stably attached thereto. The stability of the attachments of the micro-components to the beads (i.e., as in FIG. 5B formed as illustrated in 5A) was tested by incubating beads with attached micro-components in various chemicals/solvents for 24 hours. In particular, beads prepared as in FIG. 5A were incubated in 10% acetic acid in $H_2O$, Dimethylformamide, 10% ammonium hydroxide in $H_2O$, dimethyl sulfoxide, phosphate buffered saline, methanol, $H_2O$, or isopropyl alcohol for 24 hours. The micro-components remained attached to the beads in all conditions, demonstrating the suitability for use of such beads in assays described herein.

Figure 5C:
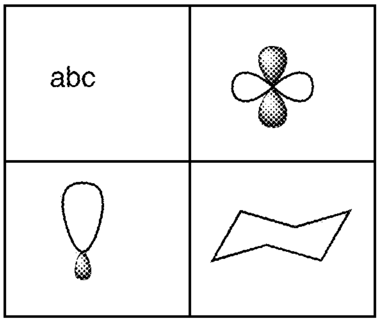

Since the beads (and the wells they were in) are transparent, the encoded micropuck can be imaged by brightfield microscopy regardless of orientation. The visibly distinguishable code is not particularly limited other than by the size of the micro-component and fabrication techniques. FIG. 5C shows an example of a 4 quadrant code, where each quadrant may include different information, potentially about the experiment and/or bead or conditions subject thereto.

Figure 5D:
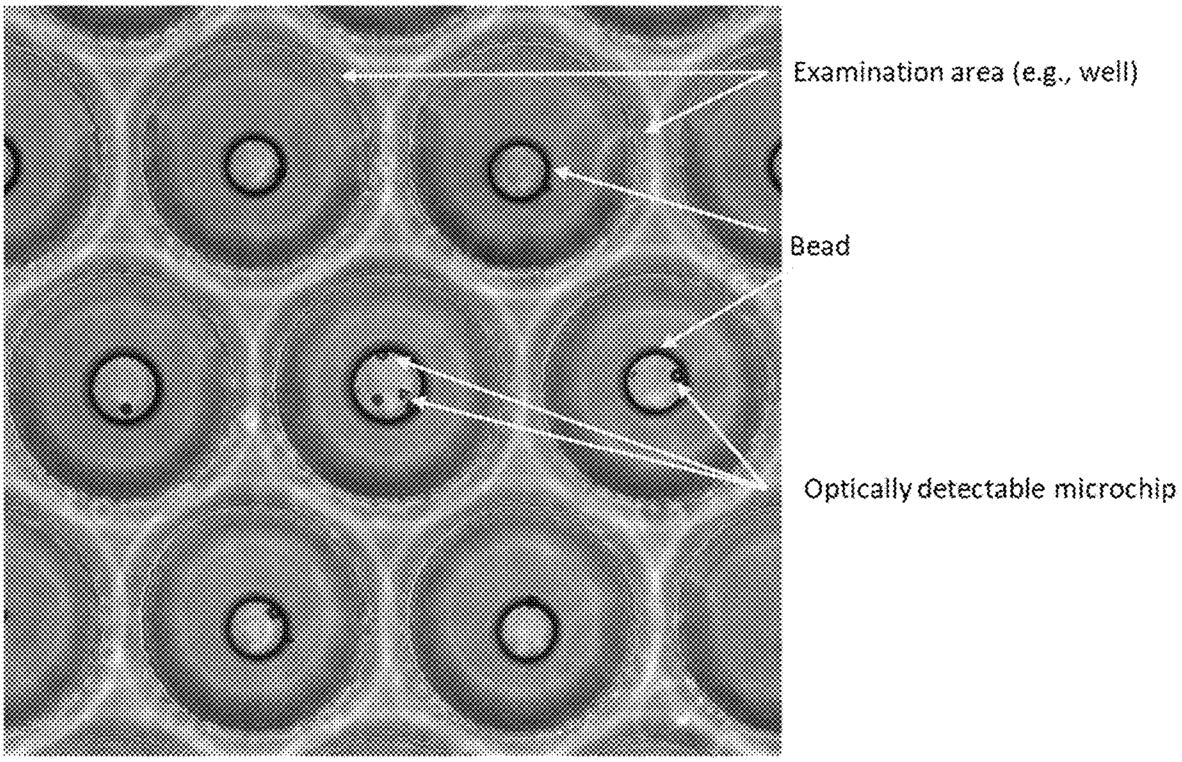

FIG. 5D shows an example of microbeads with one or more optically detectable microchips attached thereto in individual examination areas (wells) of a multi-well assay device. FIG. 5D illustrates an example where the set and specific distribution of optically detectable microchips on each bead are unique to that bead. The optically detectible microchips in FIG. 5D are in a variety of shapes and sizes and were allowed to randomly attach to the beads, resulting in distinguishable random distributions of different size/shapes of microchips attached to beads. The beads and wells were transparent, making it possible to image the microchips on the beads by bright-field microscopy or other standard imaging techniques.

To prepare the beads in FIG. 5D, microfabricated silica microchips were first re-suspended in isopropanol at a concentration equivalent to ~250,000 units per mL. 2 mL of the microchip suspension was gently mixed with 3.5 mg (approximately 168,000 units) of 30 microns NH2-Tentagel perturbation/capture beads in a 15 mL falcon tube, and the mixture was rocked for 12 hours. The falcon tube was then spun down at 20,000 relative centrifugal force (rcf) for 2 minutes, and the supernatant was discarded. A fresh 2 mL of the microchip suspension was added to the beads, and the incubation and spinning were repeated once again. After the mixture was spun down the second time, the beads with random sets of microchips attached thereto were resuspended in pure isopropanol. The resulting optically detectable microchip-bead conjugates were stored at +4° C. until further loaded into examination areas. Once in the examination areas, the beads and specific distribution of different microchips that uniquely identify the beads were imageable by brightfield microscopy, regardless of orientation due to the transparent beads.

Figure 6:
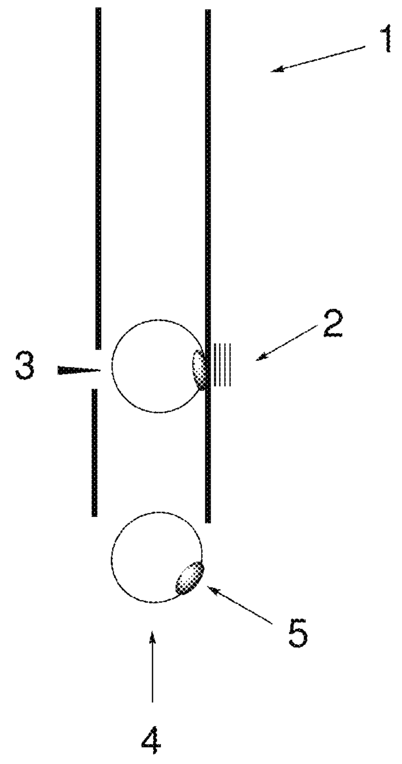
FIG. 6 illustrates the labeling area of a labeling device.

Also, or alternatively, FIG. 6 illustrates a labeling method that self-orients a ferromagnetic doped perturbation bead, 4, traveling up (or down) into the labeling site of shaft 1 of the labeling device (not shown). The initial position of the doped portion of the bead, 4, is out of sync with the desired position which is required to ensure that all of the labels applied are in a common surface area of the bead in order to image the labels on the bead for the register. As the bead approaches the labeling site, a reversible magnet, 2, positioned on the wall opposite the labeling nozzle, 3, is activated. Upon activation, perturbation bead, 4, orients the ferromagnetic portion to align with the magnet thereby allowing the labeling nozzle to label in the same approximate area of the perturbation bead.

Adding a Label Corresponding to a Compound Attached Thereon

FIGS. 7A-7C show an example of adding labels (e.g., microchips) and corresponding compounds and/or compound building blocks to a bead. Beads shown in FIGS. 7A-7B were fabricated to have optically detectible microchips of different shapes randomly attached thereto. FIG. 7A shows a wide-view image (left) and close-up image (right) of such beads in a reaction vessel (well of a 96 well plate). About 3.5 mg (~168,000) of 30 um $NH_2$-TENTAGEL™ capture beads were added to each well of a 96-well plate. To prepare resin with photocleavable linkers, TENTAGEL™ M NH2, 10 μm dia. (dry), 10 mg, 0.23 mmol/g was loaded into a spin column and swelled in DMF (1 h, RT). The resin was then reacted (3 h, 70° C., ×2) with 4-(Fmoc-aminomethyl)-3-nitrobenzoic acid (20 mM, 3.6 eq.) and DIC (20 mM, 3.6 eq.) and washed with DMF (3×0.6 mL). The fmoc-protected resin was deprotected with 20% piperidine in DMF (15 min, RT) and washed with DMA.

To prepare the microchip-bead conjugates, microfabricated silica microchips of a given shape were first re-suspended in isopropanol at a concentration equivalent to ~250,000 units per mL. Separate suspensions were prepared with unique shapes of microchips per tube. Then 2 mL of the microchip suspension was added to each well of the 96 well plate and gently mixed with the beads by rocking for 2 hours. The plate was spun down at 20,000 rcf for 2 minutes, and the supernatant was discarded. This operation was repeated twice. The medium was exchanged to Dimethylacetamide (DMA). The previously added unique one or more micro components optically encode the building block information.

For peptide couplings used to conjugate the building blocks, standard conjugation conditions and washes are employed, for instance coupling is performed with DIC (N,N'-Diisopropylcarbodiimide) with building blocks suspended in DMF (N,N-dimethylformamide). Detailed protocols of conjugation reaction are available in the supplementary information section of the publication https://doi.org/10.1021/ac500693r. Example building blocks used were: tetramethylrhodamine (TRITC) (FIGS. 7B-7C); Dasatinib metabolite m6, i.e., Dasatinib carboxylic acid—2-(4-(6-((5-((2-chloro-6-methylphenyl)carbamoyl)thiazol-2-yl)amino)-2-methylpyrimidim-4-yl)piperazin-1-yl)acetic acid; JQ1 acid—((S)-tert-butyl 2-(4-(4-chlorophenyl)-2,3,9-trimethyl-6H-thieno[3,2-f] [1,2,4]triazolo[4,3-a] [1,4]diazepin-6-yl) acetic acid); HPK1 inhibitor derivative—4-{[2-Fluoro-6-(trifluoromethyl)phenyl]amino}-2-[(6-methoxy-2-methyl-1,2,3,4-tetrahydro-7-isoquinolinyl)amino]-5-pyrimidine-5-carboxylic acid; and LNI, lenalidomide acid—2-(2,6-dioxopiperidin-3-yl)-1-oxoisoindoline-5-carboxylic acid (FIG. 7D).

FIG. 7B shows brightfield and fluorescent images of beads formed as described above and, with triangular or circular microchips as optically detectible labels and tetramethylrhodamine (TRITC) as an example building block added to labeled beads as in FIG. 7C. FIG. 7B demonstrates sequential labeling of a bead with an optically detectable label, followed by addition of a compound as an example building block without losing the optically detectible label.

Figure 7D:
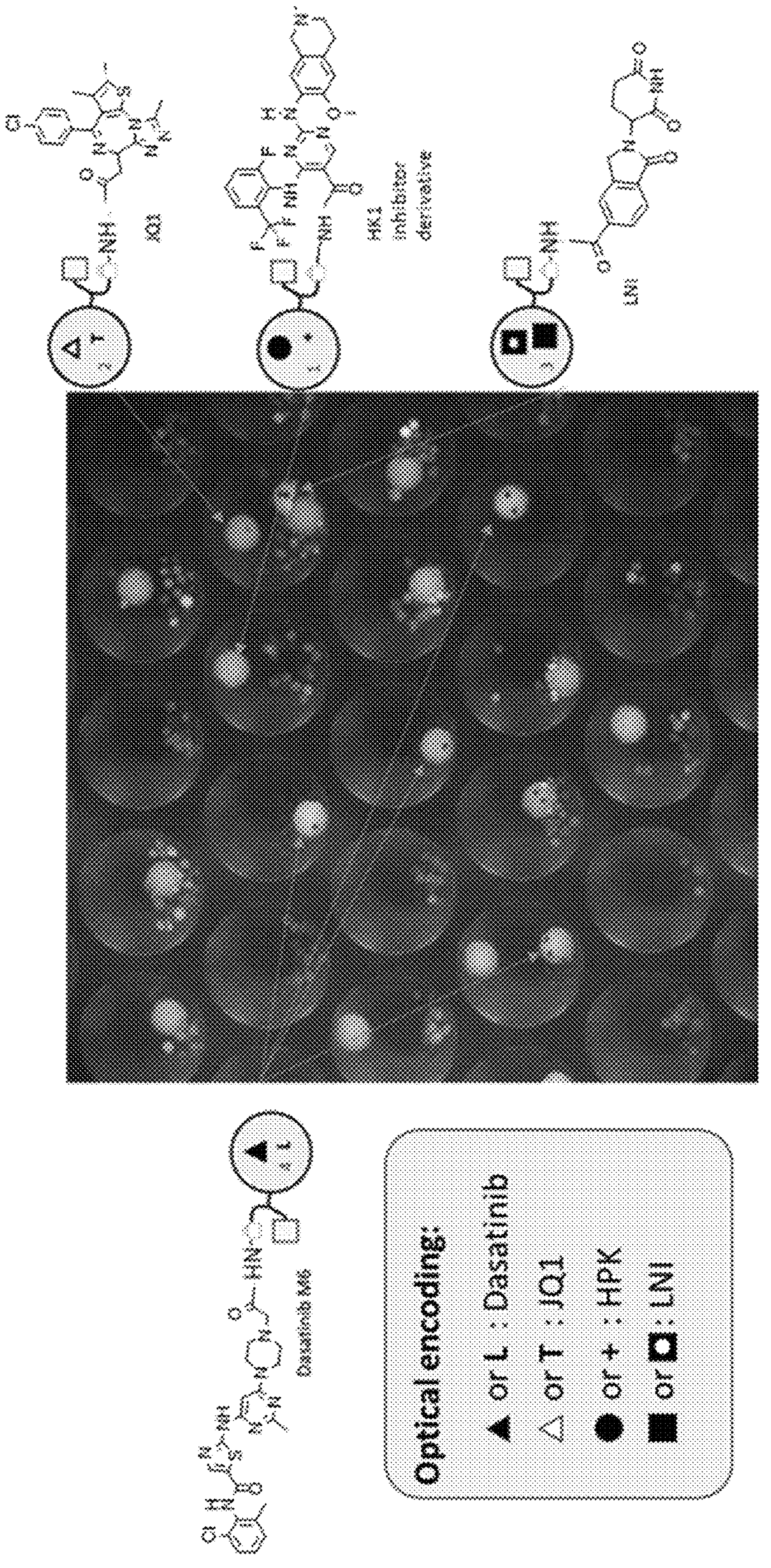

FIG. 7D shows the results of adding beads prepared as above to have optically distinguishable labels corresponding to one of 4 building blocks/compounds (Dasatinib, JQ1, HPK and LNI). Individual beads were added to wells of a multiwell assay device. Jurkat cells engineered to have enhanced green fluorescent protein (eGFP) reporter fused to nuclear factor of activated T cells (NFAT) transcription factor were added to each well (cells purchased from BPS Bioscience, Catalog #78384). The compounds were released from the beads by exposure to 10 seconds of 365 nm wavelength light having illumination power of 60 $mW/cm^2$ and allowed to interact with the cells in the respective wells. Cells exposed to JQ1, HPK, and LNI (identified by the corresponding optically detectible labels of the perturbation beads imaged in each cell) showed minimal change in the NFAT-eGFP expression levels, whereas cells exposed to Dasatinib showed almost complete downregulation of eGFP. This exemplifies using optically detectible labels on the bead to code for perturbation compounds and/or building blocks and corresponding that visible code to a cell perturbation.

Assay Preparation

A cell (e.g., a human cell, such as a HeLa cell) is then selected as the cell to be perturbed in the assay. A cell, a perturbation bead, and a capture bead are combined into a single examination area of a mapped assay device, (e.g., such as the assay device depicted as in FIG. 1A or 1B) containing an aqueous composition suitable for conducting the assay.

The Assay

The combination of components provides for the following in a single examination well was illustrated in Reaction Scheme 2 above and is repeated below:

REACTION SCHEME 2

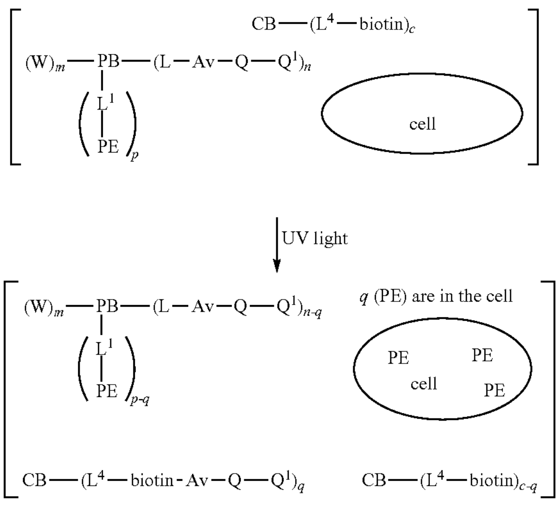

After combining these components into an examination area of a mapped assay device also having other so filled examination areas, then at any time during the assay, a register is created by taking a digital picture of the assay device including each of the examination areas which register records the uniquely labeled perturbation bead in each examination area preferably in electronic form. In some embodiments, the picture is taken from multiple angles using a confocal lens and a transparent assay device.

The assay is initiated by releasing at least a portion of the perturbation compound from the perturbation bead into the assay solution to allow the perturbation compound to interface with the cell. When the perturbation oligonucleotide is attached to the perturbation bead via a releasable bond which, for the sake of illustration, is the same releasable bond or group attaching the perturbation compound to the perturbation bead, then application of an appropriate stimulus such as UV light will result in at least a portion of both the perturbation compound and the perturbation oligonucleotide being released into the assay solution.

In an example, A549 cells were screened against a BRD4 focused, ~10,000 member DNA-encoded (poly-T tailed) combinatorial library synthesized at the end of a nitrobenzyl linker attached to beads. Individual perturbation beads were deposited into corresponding micro-wells with a diameter of 130 m and 130 m depth, across a chip containing ~47,000 wells. 5-10 cells were then added to each of the wells, which were then oil-capped with oil. Compounds were UV-cleaved from the beads to target a concentration of ~5 μM and the chip was incubated for 24 hours in a 37° C. incubator. After the 24-hour incubation, the cells were lysed via freeze-thaw: −80° C. for 30 minutes and thawed for 45 minutes. Released mRNA were hybridized to the barcoded dT oligos on the same beads (perturbation bead acting simultaneously as capture bead). The oil-caps were removed by washing the chip with a series of low-salt washes, protease digestion, and high-salt washes. The mRNA hybridized beads were removed from the chip and reverse transcription was performed. The beads were then split into eight whole-transcriptome amplification reactions. Libraries were generated via tagmentation of Nextera-B transposons and subsequent index-polymerase chain reaction (PCR). The captured nucleic acids from the cells were sequenced at ~25,000 reads per well.

In a parallel chip, hits were identified by fluorescent microscopy. Briefly, cells were fixed 4% paraformaldehyde (PFA) for 30 min at room temperature (RT) and permeabilized 0.5% triton x-100. Cells were blocked with 5% bovine serum albumin (BSA) with 0.2% triton for 40 minutes and then stained with BRD4 and B-tubulin antibodies for 2 hour at RT and subsequent secondary antibodies and Hoechst (nuclear) staining for 2 hours at RT. The chip was imaged and hits identified by BRD4/tubulin vs BRD4/nuclear ratio. The "hits" were picked from the chip and amplified with Illumina P5/P7 primers. Libraries were sequenced at ~10, 000 reads per bead to identify the bead barcode/compound identifier oligonucleotide.

Figure 8A:
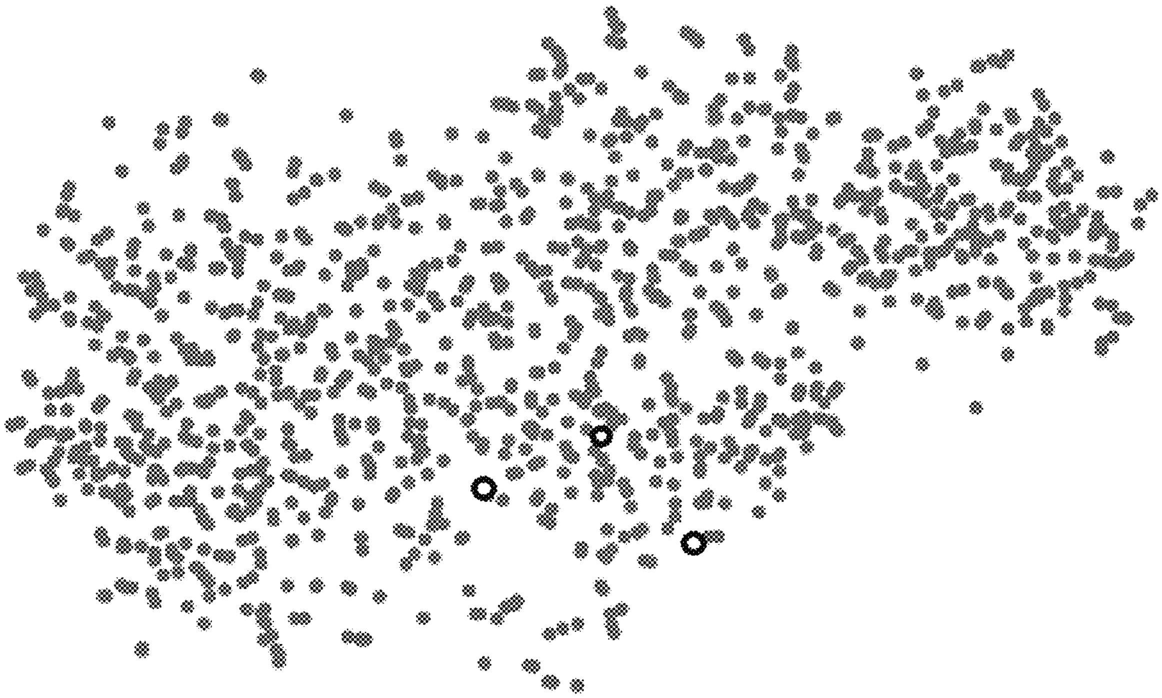
FIGS. 8A-8B show the results of an assay to determine compounds in a combinatorial library that actively perturb A549 cells.
Figure 8B:
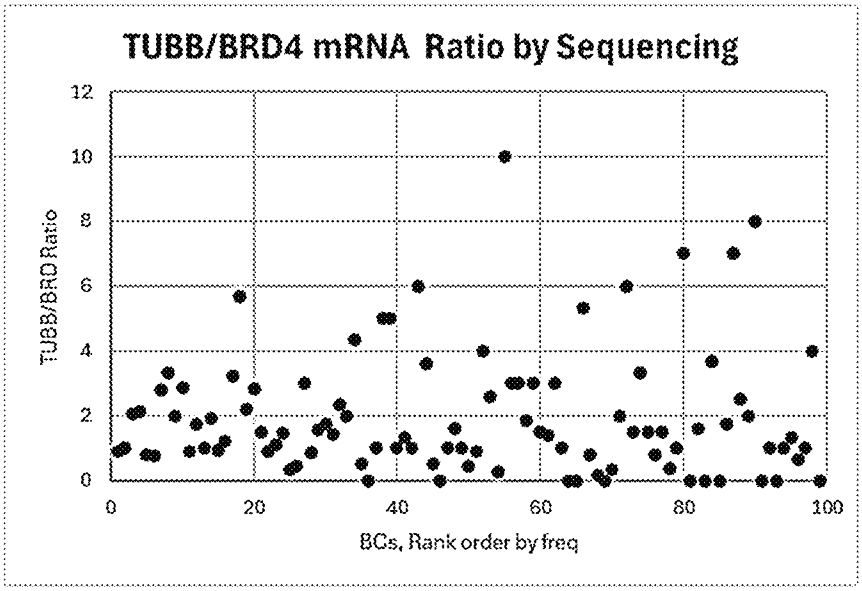

FIGS. 8A and 8B show the results of sequencing captured oligo from this example. mRNA-seq libraries were analyzed by first mapping using STAR (Systems Transcriptional Activity Reconstruction, e.g., Wang et al., Bioinformatics, Volume 29, Issue 24, December 2013, Pages 3204-3210, doi.org/10.1093/bioinformatics/btt558) on the hg38 annotated genome. Unique molecular identifiers (UMIs) were calculated to ensure accurate quantification of gene expression levels. Pre-processing steps were included to remove beads containing high mitochondrial and ribosomal content, and gene expression was normalized to house-keeping genes. Dimensionality reduction techniques were applied to visualize the results on a two-dimensional plot based on transcriptomic similarity (t-distributed stochastic neighbor embedding plot in FIG. 8A). Hits identified from the fluorescent microscopy imaging were overlayed (empty circles in FIG. 8A) and TUBB/BRD4 mRNA ratios calculated by sequencing (FIG. 8B). It is observed that compounds that cause decreased BRD4 levels by imaging upregulate BRD4 mRNA levels, suggesting a feedback loop that compensates for protein degradation by first increasing mRNA expression.

In some embodiments, the bead employed can be doped with a ferromagnetic material which can be used as an orienting component. For example, FIG. 6 illustrates a self-orienting aspect of a ferromagnet doped perturbation bead, 4, traveling up (or down) into the labeling site of shaft 1 of the labeling device (not shown).

In addition, perturbation beads added to the examination area can be oriented by placing a magnet under the assay device which then realigns the bead so that the labels are pointing substantial upward for imaging purposes.

Each of the assays conducted in the mapped assay device is incubated at standard conditions allowing the released compounds to perturb the cell. During the assay, pictures encompassing each assay well are taken at periodic intervals. Such pictures can evidence a change in cellular morphology as evidence by a changed cell shape and other possible attributes. Possible changes in cellular morphology include distortions of cell shape. For example, if the cell has an original elliptical shape and is distorted by the perturbation into a shape that somewhat resembles an elliptical shape, but which also evidences areas of undulations and bulging due to the perturbation caused by the perturbation compounds. These changes captured during the assay are deemed to reflect dynamic functional changes in the perturbed cell.

Upon completion of the assay, the cell is lysed in the presence of the perturbation bead which captures perturbation components generated by the cell during the assay. Using the perturbation bead as described above, the perturbation components of interest in the cellular milieu are captured on the capture bead as are the compound oligonucleotides as shown in Reaction Scheme 2 above.

In some embodiments, each of the mRNA, the compound oligonucleotide, and the label oligonucleotide (if separate from the compound oligonucleotide) are sequenced either on the capture bead or separated from the capture bead by cleaving the cleavable bonds using an appropriate cleavage stimulation. The changes in the mRNA evidenced by the perturbation can be combined with any dynamic changes in cellular functionality as noted above to enhance the more of the changes in cellular functionality generated by the perturbation.

The changes in nucleic acids expressed by the lysed cell can be correlated to the photography or videography conducted for the examination area from where the cell was lysed as described in detail above.

9. EMBODIMENTS

Each of the following embodiments are representative of a portion of the possible combinations that can be achieved herein many of which are explicitly provided above.

Embodiment 1: A perturbation bead for use in an assay conducted in an assay device said perturbation bead comprising a detectable label or a set of detectable labels attached to said bead which uniquely identifies the perturbation bead in said assay device.

Embodiment 2: A perturbation bead for use in an assay conducted in an examination area in a mapped assay device said perturbation bead comprising a detectable label or a set of detectable labels attached to said bead which uniquely identifies the perturbation bead in said assay device.

Embodiment 3: A perturbation bead for use in an assay conducted in an examination area in a mapped assay device comprising multiple examination areas, said perturbation bead comprising a detectable label or a set of detectable labels attached to said bead which uniquely identifies the perturbation bead in said assay device wherein the perturbation bead in said mapped assay device is correlated to a specific examination area thereby identifying that examination area where said perturbation bead is located.

Embodiment 4: A perturbation bead for use in an assay conducted in an examination area in a mapped assay device said perturbation bead comprising a detectable label or a set of detectable labels attached to said bead which uniquely identifies the perturbation bead in said assay device and said examination area in said mapped assay device is correlated to said perturbation bead wherein said correlation is memorialized.

Embodiment 5: A perturbation bead for use in an assay conducted in an examination area in a mapped assay device said perturbation beads comprise a detectable label or a set of detectable labels attached to said bead which uniquely identifies the perturbation bead in said assay device and said examination area in said mapped assay device is correlated to said perturbation bead and said correlation is memorialized into a registry recording the position of perturbation bead in each examination area in the mapped assay device.

Embodiment 6: A perturbation bead for use in an assay conducted in an assay device said perturbation bead comprising an optically detectable label or a set of optically detectable labels attached to said bead which uniquely identifies the perturbation bead in said assay device.

Embodiment 7: A perturbation bead for use in an assay conducted in an examination area in a mapped assay device said perturbation bead comprises an optically detectable label or a set of optically detectable labels attached to said bead which uniquely identifies the perturbation bead in said assay device.

Embodiment 8: A perturbation bead for use in an assay conducted in an examination area in a mapped assay device comprising multiple examination areas, said perturbation bead comprises an optically detectable label or a set of optically detectable labels attached to said bead which uniquely identifies the perturbation bead in said assay device wherein the perturbation bead in said mapped assay device is correlated to a specific examination area thereby identifying that examination area where said perturbation bead is located.

Embodiment 9: A perturbation bead for use in an assay conducted in an examination area in a mapped assay device said perturbation bead comprises an optically detectable label or a set of optically detectable labels attached to said bead which uniquely identifies the perturbation bead in said assay device and said examination area in said mapped assay device is correlated to said perturbation bead wherein said correlation is memorialized.

Embodiment 10: A perturbation bead for use in an assay conducted in an examination area in a mapped assay device said perturbation bead comprises an optically detectable label or a set of optically detectable labels attached to said bead which uniquely identifies the perturbation bead in said assay device and said examination area in said mapped assay device is correlated to said perturbation bead and said correlation is memorialized into a registry recording the position of each perturbation bead in each examination area in the mapped assay device.

Embodiment 11: A perturbation bead for use in an assay conducted in an assay device said perturbation bead comprising a set of detectable labels attached to said bead and a multiplicity of the same perturbation oligonucleotide releasably bound thereto which identifies the perturbation element and the unique set of labels.

Embodiment 12: A perturbation bead for use in an assay conducted in an examination area in a mapped assay device said perturbation bead comprising a set of detectable labels associated with said bead which uniquely identifies the bead in said examination area of said assay device and a multiplicity of the same perturbation oligonucleotide releasably bound thereto which identifies the perturbation element and the unique set of labels.

Embodiment 13: A perturbation bead for use in an assay conducted in an examination area in a mapped assay device comprising multiple examination areas, said perturbation bead comprising a set of detectable labels attached to said bead which uniquely identifies the perturbation bead in said assay device wherein the perturbation bead in said mapped assay device is correlated to a specific examination area thereby identifying that examination area where said perturbation bead is located and a multiplicity of the same perturbation oligonucleotide releasably bound thereto which identifies the perturbation element and the unique label or set of labels.

Embodiment 14: A perturbation bead for use in an assay conducted in an examination area in a mapped assay device said perturbation bead comprises a set of detectable labels attached to said bead which uniquely identifies the perturbation bead in said assay device and said examination area in said mapped assay device is correlated to said perturbation bead wherein said correlation is memorialized and a multiplicity of the same perturbation oligonucleotide releasably bound thereto which identifies the perturbation element and the unique label or set of labels.

Embodiment 15: A perturbation bead for use in an assay conducted in an examination area in a mapped assay device said perturbation bead comprising a set of detectable labels attached to said bead which uniquely identifies the perturbation bead in said assay device and said examination area in said mapped assay device is correlated to said perturbation bead and said correlation is memorialized into a register recording the position of each perturbation bead in each examination area in the mapped assay device and a multiplicity of the same perturbation oligonucleotide releasably bound thereto which identifies the perturbation element and the unique label or set of labels.

Embodiment 16: A perturbation bead for use in an assay conducted in an assay device said perturbation bead comprising a set of optically detectable labels attached to said bead which uniquely identifies the perturbation bead in said assay device and a multiplicity of the perturbation oligonucleotide releasably bound thereto which identifies the perturbation element and the unique set of labels.

Embodiment 17: A perturbation bead for use in an assay conducted in an examination area in a mapped assay device said perturbation bead comprises a set of optically detectable labels attached to said bead which uniquely identifies the perturbation bead in said assay device and a multiplicity of the same perturbation oligonucleotide releasably bound thereto which identifies the perturbation element and the unique label or set of labels wherein said perturbation oligonucleotide comprises a binding element that captures nucleic acids.

Embodiment 18: A perturbation bead for use in an assay conducted in an examination area in a mapped assay device comprising multiple examination areas, said perturbation bead comprises a set of optically detectable labels attached to said bead which uniquely identifies the perturbation bead in said assay device wherein the perturbation bead in said mapped assay device is correlated to a specific examination area thereby identifying that examination area where said perturbation bead is located and a multiplicity of the same perturbation oligonucleotide releasably bound thereto which identifies the perturbation element and the unique label or set of labels.

Embodiment 19: A perturbation bead for use in an assay conducted in an examination area in a mapped assay device said perturbation bead comprises a set of optically detectable labels attached to said bead which uniquely identifies the perturbation bead in said assay device and said examination area in said mapped assay device is correlated to said perturbation bead wherein said correlation is memorialized into a registry and a multiplicity of the same perturbation oligonucleotide releasably bound thereto which identifies the perturbation element and the unique label or set of labels.

Embodiment 20: A perturbation bead for use in an assay conducted in an examination area in a mapped assay device said perturbation bead comprises a set of optically detectable labels attached to said bead which uniquely identifies the perturbation bead in said assay device and said examination area in said mapped assay device is correlated to said perturbation bead and said correlation is memorialized into a searchable registry recording the position of each perturbation bead in each examination area in the mapped assay device and a multiplicity of the same perturbation oligonucleotide releasably bound thereto which identifies the perturbation element and the unique label or set of labels.

Embodiment 21: A population of perturbation beads for use in an assay conducted in an assay device where each of said perturbation beads comprises a detectable label or a set of detectable labels attached to said bead which uniquely identifies the perturbation bead in said assay device.

Embodiment 22: A population of perturbation beads for use in an assay conducted in an assay device where each of said perturbation beads comprises a detectable label or a set of detectable labels attached to said bead which uniquely identifies the perturbation bead in said assay device.

Embodiment 23: A population of perturbation beads for use in an assay conducted in an examination area in a mapped assay device comprising multiple examination areas, each of said perturbation bead comprising a detectable label or a set of detectable labels attached to said bead which uniquely identifies the perturbation bead in said assay device wherein the perturbation bead in said mapped assay device is correlated to a specific examination area thereby identifying that examination area where said perturbation bead is located.

Embodiment 24: A population of perturbation beads for use in an assay conducted in an examination area in a mapped assay device where each of said perturbation beads comprises a detectable label or a set of detectable labels attached to said bead which uniquely identifies the perturbation bead in said assay device and said examination area in said mapped assay device is correlated to said perturbation bead wherein said correlation is memorialized.

Embodiment 25: A population of perturbation beads for use in an assay conducted in an examination area in a mapped assay device where each of said perturbation beads comprises a detectable label or a set of detectable labels attached to said bead which uniquely identifies the perturbation bead in said assay device and said examination area in said mapped assay device is correlated to said perturbation bead and said correlation is memorialized into a registry recording the position of perturbation bead in each examination area in the mapped assay device.

Embodiment 26: A population of perturbation beads for use in an assay conducted in an assay device where each of said perturbation beads comprises an optically detectable label or a set of optically detectable labels attached to said bead which uniquely identifies the perturbation bead in said assay device.

Embodiment 27: A population of perturbation beads for use in an assay conducted in an examination area in a mapped assay device where each of said perturbation bead comprises an optically detectable label or a set of optically detectable labels attached to said bead which uniquely identifies the perturbation bead in said assay device.

Embodiment 28: A population of perturbation beads for use in an assay conducted in an examination area in a mapped assay device comprising multiple examination areas, each of said perturbation beads comprises an optically detectable label or a set of optically detectable labels attached to said bead which uniquely identifies the perturbation bead in said assay device wherein the perturbation bead in said mapped assay device is correlated to a specific examination area thereby identifying that examination area where said perturbation bead is located.

Embodiment 29: A population of perturbation beads for use in an assay conducted in an examination area in a mapped assay device, each of said perturbation beads comprises an optically detectable label or a set of optically detectable labels attached to said bead which uniquely identifies the perturbation bead in said assay device and said examination area in said mapped assay device is correlated to said perturbation bead wherein said correlation is memorialized.

Embodiment 30: A population of perturbation beads for use in an assay conducted in an examination area in a mapped assay device, each of said perturbation beads comprises an optically detectable label or a set of optically detectable labels attached to said bead which uniquely identifies the perturbation bead in said assay device and said examination area in said mapped assay device is correlated to said perturbation bead and said correlation is memorialized into a registry recording the position of each perturbation bead in each examination area in the mapped assay device.

Embodiment 31: A population of perturbation beads for use in an assay conducted in an assay device, each of said perturbation beads comprises a set of detectable labels attached to said bead and a multiplicity of the same perturbation oligonucleotide releasably bound thereto which identifies the perturbation element and the unique set of labels.

Embodiment 32: A population of perturbation beads for use in an assay conducted in an examination area in a mapped assay device, each of said perturbation beads comprises a set of detectable labels associated with said bead which uniquely identifies the bead in said examination area of said assay device and a multiplicity of the same perturbation oligonucleotide releasably bound thereto which identifies the perturbation element and the unique set of labels.

Embodiment 33: A population of perturbation beads for use in an assay conducted in an examination area in a mapped assay device comprising multiple examination areas, each of said perturbation beads comprises a set of detectable labels attached to said bead which uniquely identifies the perturbation bead in said assay device wherein the perturbation bead in said mapped assay device is correlated to a specific examination area thereby identifying that examination area where said perturbation bead is located and a multiplicity of the same perturbation oligonucleotide releasably bound thereto which identifies the perturbation element and the unique label or set of labels.

Embodiment 34: A population of perturbation beads for use in an assay conducted in an examination area in a mapped assay device, each of said perturbation beads comprises a set of detectable labels attached to said bead which uniquely identifies the perturbation bead in said assay device and said examination area in said mapped assay device is correlated to said perturbation bead wherein said correlation is memorialized and a multiplicity of the same perturbation oligonucleotide releasably bound thereto which identifies the perturbation element and the unique label or set of labels.

Embodiment 35: A population of perturbation beads for use in an assay conducted in an examination area in a mapped assay device, each of said perturbation beads comprises a set of detectable labels attached to said bead which uniquely identifies the perturbation bead in said assay device and said examination area in said mapped assay device is correlated to said perturbation bead and said correlation is memorialized into a registry recording the position of each perturbation bead in each examination area in the mapped assay device and a multiplicity of the same perturbation oligonucleotide releasably bound thereto which identifies the perturbation element and the unique label or set of labels.

Embodiment 36: A population of perturbation beads for use in an assay conducted in an assay device, each of said perturbation beads comprises a set of optically detectable labels attached to said bead which uniquely identifies the perturbation bead in said assay device and a multiplicity of the perturbation oligonucleotide releasably bound thereto which identifies the perturbation element and the unique set of labels.

Embodiment 37: A population of perturbation beads for use in an assay conducted in an examination area in a mapped assay device, each of said perturbation beads comprises a set of optically detectable labels attached to said bead which uniquely identifies the perturbation bead in said assay device and a multiplicity of the same perturbation oligonucleotide releasably bound thereto which identifies the perturbation element and the unique label or set of labels wherein said perturbation oligonucleotide comprises a binding element that captures nucleic acids.

Embodiment 38: A population of perturbation beads for use in an assay conducted in an examination area in a mapped assay device comprising multiple examination areas, each of said perturbation beads comprises a set of optically detectable labels attached to said bead which uniquely identifies the perturbation bead in said assay device wherein the perturbation bead in said mapped assay device is correlated to a specific examination area thereby identifying that examination area where said perturbation bead is located and a multiplicity of the same perturbation oligonucleotide releasably bound thereto which identifies the perturbation element and the unique label or set of labels.

Embodiment 39: A population of perturbation beads for use in an assay conducted in an examination area in a mapped assay device, each of said perturbation beads comprises a set of optically detectable labels attached to said bead which uniquely identifies the perturbation bead in said assay device and said examination area in said mapped assay device is correlated to said perturbation bead wherein said correlation is memorialized into a registry and a multiplicity of the same perturbation oligonucleotide releasably bound thereto which identifies the perturbation element and the unique label or set of labels.

Embodiment 40: A population of perturbation beads for use in an assay conducted in an examination area in a mapped assay device, each of said perturbation beads comprises a set of optically detectable labels attached to said bead which uniquely identifies the perturbation bead in said assay device and said examination area in said mapped assay device is correlated to said perturbation bead and said correlation is memorialized into a searchable registry recording the position of each perturbation bead in each examination area in the mapped assay device and a multiplicity of the same perturbation oligonucleotide releasably bound thereto which identifies the perturbation element and the unique label or set of labels.

Embodiment 41: A perturbation bead according to any one of Embodiments 1 through 20, which further comprises a first binding element that is complementary to and associates with a binding element on a capture bead; and a second binding element or a group that can be derivatized to a second binding element which is complementary to and associates with one or more perturbation components released by a lysed cell.

Embodiment 42: A population of perturbation beads according to any one of Embodiments 21 through 40, where each perturbation bead further comprises a first binding element that is complementary to and associates with a binding element on a capture bead; and a second binding element or a group that can be derivatized to a second binding element which is complementary to and associates with one or more perturbation components released by a lysed cell.

Embodiment 43: A perturbation bead according to any one of Embodiments 1 through 20, which further comprises a capture bead positioned in a specific examination area of a mapped assay device.

Embodiment 44: A population of perturbation beads according to any one of Embodiments 21 through 40, where each perturbation bead further comprises a capture bead positioned in a specific examination area of a mapped assay device.

Embodiment 45: A perturbation bead according to according to Embodiments 1-42, wherein said perturbation bead is represented by the formula:

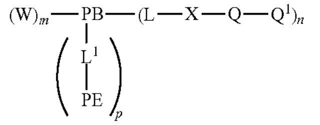

(I)

where:

W is an optically detectable label or a set of optically detectable labels that uniquely identify the perturbation bead;

PB is a perturbation bead;

PE is a perturbation element;

L is a releasable linker;

$L^1$ is a releasable linker which may be the same or different from L, and when different, L and $L^1$ may be cleaved with the same stimulus or with different stimuli;

Q is a perturbation oligonucleotide that codes for the perturbation element and the unique label or set of labels;

$Q^1$ is a binding element;

m is an integer from 1 to 100 (or more, depending on the type of label and/or size of bead);

n represents the multiplicity of such (L Q-$Q^1$) groups bound to the perturbation bead; and p represents the multiplicity of such (PE) groups bound to the perturbation bead.

Embodiment 46: A population of perturbation beads according to any one of Embodiments 1-42, wherein each of said perturbation beads in said population is represented by the formula:

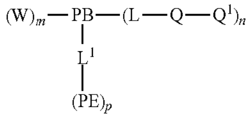

where:

W is an optically detectable label or a set of optically detectable labels that uniquely identify the perturbation bead;

PB is a perturbation bead;

PE is a perturbation element;

L is a releasable linker;

$L^1$ is a releasable linker which may be the same or different from L and when different, L and $L^1$ may be cleaved with the same stimulus or with different stimuli;

Q is a perturbation oligonucleotide that codes for the perturbation element and the unique label or set of labels;

$Q^1$ is a binding element;

m is an integer from 1 to 10;

n represents the multiplicity of such (L-Q-$Q^1$) groups bound to the perturbation bead; and p represents the multiplicity of such (PE) groups bound to the perturbation bead.

Embodiment 47: A population of perturbation beads according to any one of Embodiments 1 to 42, wherein each of said perturbation beads in said population is represented by the formula:

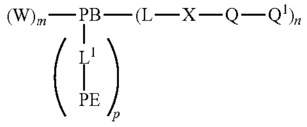

where:

W is an optically detectable label or a set of optically detectable labels that uniquely identify the perturbation bead;

PB is a perturbation bead;

PE is a perturbation element;

L is a releasable linker;

$L^1$ is a releasable linker which may be the same or different from L, and when different, L and $L^1$ may be cleaved with the same stimulus or with different stimuli;

Q is a perturbation oligonucleotide that codes for the perturbation element and the unique label or set of labels;

$Q^1$ is a binding element;

X is a binding element;

m is an integer from 1 to 100 (or more, depending on the type of label and/or size of bead);

n represents the multiplicity of such (L-X-Q-$Q^1$) groups bound to the perturbation bead; and p represents the multiplicity of such (PE) groups bound to the perturbation bead.

Embodiment 48: A population of perturbation beads wherein said population comprises perturbation beads according to Embodiment 46.

Embodiment 49: A perturbation bead according to Embodiments 45 and 47 wherein each of p and n independently range up to about $6.02\times10^{17}$.

Embodiment 50: A population of perturbation beads according to Embodiments 46 and 48 wherein each of p and n independently range up to about $6.02\times10^{17}$.

Embodiment 51: A combination of a perturbation bead with a capture bead said combination comprises a perturbation bead as described in any one of embodiments 1 through 20 and a capture bead comprises multiple copies of a capturing element releasably bound thereto.

Embodiment 52: A combination of a perturbation bead with a capture bead wherein said specific combination of said perturbation bead and said capture bead is included in a register that memorializes the combination including the unique code found on at least one of the beads:

provided that:

a) if said perturbation bead comprises a unique label or set of labels, then said label or labels are coded by a unique oligonucleotide which is optionally incorporated into or onto the perturbation oligonucleotide;

b) if the perturbation oligonucleotide does not code for said label or labels, then the perturbation bead further comprises a label oligonucleotide releasably attached to said perturbation bead and which codes for said label or labels then said label oligonucleotide is releasably attached to said perturbation bead and said released label oligonucleotide and said perturbation oligonucleotide are attachable to each other;

c) if the capture bead comprises a unique label or set of labels, the capture bead does not contain a set of oligonucleotides that are bound to the bead and code for said label wherein said perturbation oligonucleotide or a said label oligonucleotide is releasably attached to said perturbation bead and said released label oligonucleotide and said perturbation oligonucleotide are attachable to each other;

d) if the capture element of said capture bead captures said perturbation oligonucleotide which, in turn, comprises a label oligonucleotide, then said perturbation oligonucleotide further comprises a capture element for capturing cellular nucleic acids; and e) if the nucleic acids are captured on the capture bead and the perturbation bead is labeled but lacks an oligonucleotide code, then the capture bead can contain an oligonucleotide that codes for the label on the perturbation bead.

Embodiment 53: A combination of a perturbation bead with a capture bead according to Embodiment 52 wherein said capture bead self-identifies a unique perturbation bead from a population of perturbation beads which capture bead comprises a multiplicity of capture elements having bound to at least a portion thereof a perturbation oligonucleotide that codes for a perturbation element and a unique label associated with a particular perturbation bead wherein said code self-identifies said unique perturbation bead from a population of uniquely labeled perturbation beads.

Embodiment 54: A method for associating each perturbation bead found in a plurality of perturbation beads to a single examination area in a mapped assay device where a single perturbation bead is placed into a single examination area which method comprises:

a) coding each of said perturbation beads with an optically detectable label or a set of optically detectable labels unique to that bead;

b) adding a capture bead to each of the examination areas in said device comprising a perturbation bead wherein said capture bead is optionally labeled and comprises a multiplicity of capture elements releasably bound thereto;

c) associating each unique labeled perturbation bead to each examination area in said device.

Embodiment 55: The method of Embodiment 54, wherein said method further comprises:

d) memorializing each position of each perturbation bead to the specific examination area on the mapped assay device.

Embodiment 56: A method for identifying a specific examination area associated to a perturbation component released from a perturbed lysed cell in said area of an assay device comprising a multiplicity of said examination areas, which method comprises:

a) conducting an assay in each of a multiplicity of examination areas in a mapped assay device wherein each of said examination areas comprise a cell, a perturbating element for said cell in an assay solution;

b) including in each of said examination areas i) a perturbation bead which comprises:

a plurality of perturbation elements releasably bound thereto, an optically detectable label or a set of optically detectable labels attached to said bead which uniquely identifies that bead wherein said bead comprises a multiplicity of the same perturbation oligonucleotide which is unique to said perturbation bead and is attached to thereto optionally through a linker wherein said perturbation oligonucleotide codes for the structure of the perturbation element on said bead and the unique label associated with that bead; and ii) a capture bead comprising a multiplicity of capture elements releasably bound to said bead which capture elements are capable of capturing the perturbation oligonucleotide when released from the perturbation bead;

c) correlating and memorializing the unique optically detectable label or set of labels in each examination area by associating the unique optically detectible labels on said capture bead to said mapped assay device thereby providing for a 1:1 relationship between each capture bead in each of the examination areas;

d) inducing a perturbation on said cell by releasing at least a portion of the perturbation element from the perturbation bead thereby inducing a functional change in said cell which comprises at least a change evidenced by one or more perturbation components expressed by said cell;

e) releasing at least a portion of the perturbation oligonucleotide from the perturbation bead for capture by the capture element on the capture bead provided that said perturbation oligonucleotide further comprises or is modified to comprise a capture element that captures one or more perturbation components;

f) lysing said cell to release said perturbation components into said assay solution and capturing at least one of said component onto the capture element of said perturbation oligonucleotide associated with said capture bead;

g) releasing the capture element from the capture bead;

h) sequencing the oligonucleonucleotide comprising the capture element, the perturbation oligonucleotide and one or more perturbation components;

i) identifying the structure of the perturbation element and the unique label or set of labels that identify the unique perturbation bead;

j) correlating said label to a specific examination area in said mapped assay device by reference to the memorialized position of each uniquely labeled bead thereby identifying the particular examination area from which the perturbation component was retrieved.

Embodiment 57: The method of Embodiment 56, wherein said method further comprises:

k) obtaining images of each of the examination areas during the assay;

l) correlating the images to the specific examination area defined in g) above; and m) evaluating changes in cellular morphology during the assay as a result of the perturbation of the cell.

Embodiment 58: The method of Embodiment 57, wherein said method further comprises memorializing each position of each perturbation bead to the specific examination area on the mapped assay device.

Embodiment 59: A system for providing dynamic information regarding the impact of a perturbation element on a cell in an assay said system comprises:

a) a mapped assay device comprising multiple examination areas that are individually identifiable;

b) a perturbation bead comprising:

multiple copies of a perturbation element releasably bound thereto which element is unique to other perturbation beads to be used in the assay device;

a label or set of labels that uniquely identify that bead from other beads to be used in an assay; and a perturbation oligonucleotide that codes for the perturbation element as well as the label or set of labels on the perturbation bead;

c) a capture bead as described herein;

d) a cell; and e) a register that correlates each perturbation bead to a specific examination area.

Embodiment 60: The system of Embodiment 59, wherein said perturbation bead used in said system is any one of those recited in Embodiments 1-58.

Embodiment 61: The system of Embodiment 59, wherein the assay device comprises from 90 to 2,000,000 examination areas.

What is claimed is:

1. An optically labeled perturbation microbead from a combinatorial library of microbeads, wherein said optically labeled perturbation microbead comprises: a structure of Formula I';

(I')

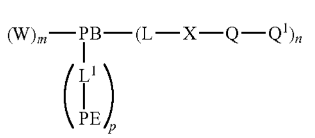

wherein:

PB is a perturbation microbead;

L and $L^1$ are each a releasable linker, wherein L and $L^1$ can be the same or different;

PE is a perturbation element comprising a chemical compound, wherein each chemical compound comprises a plurality of chemical building blocks, wherein PE is releasably bound to the perturbation microbead via the releasable linker $L^1$;

W is a set of optically detectable labels that uniquely identifies the perturbation microbead, wherein each optically detectable label or each set of optically detectable labels:

(i) is optically distinguishable from all other optically detectable labels of the set of optically detectable labels; and (ii) uniquely corresponds to a chemical building block of the plurality of chemical building blocks;

Q is a perturbation oligonucleotide that codes for the chemical compound, wherein each perturbation oligonucleotide (Q) comprises a sequence of oligonucleotide strands, wherein each oligonucleotide strand of the sequence of oligonucleotide strands uniquely codes for both:

i) a chemical building block of the plurality of chemical building blocks in each perturbation element (PE); and (ii) an optically detectable label corresponding to the chemical building block of the plurality of chemical building blocks in each perturbation element (PE);

$Q^1$ is an oligonucleotide binding element that is:

(i) complementary to a complementary capture binding element on a capture bead; or (ii) complementary to a cellular component released from a lysed cell;

m is an integer from 1 to 100, wherein m denotes a number of the sets of optically detectable labels (W) bound to the perturbation microbead (PB);

n is a number of (L-Q-$Q^1$) groups bound to the perturbation microbead (PB), wherein n is in a range from $1\times10^5$ to $6.02\times10^{17}$; and p is a number of ($L^1$-PE) groups that are bound to the perturbation microbead (PB), wherein p is in a range from $1\times10^5$ to $6.02\times10^{17}$.

2. The optically labeled perturbation microbead of claim 1, wherein the oligonucleotide binding element ($Q^1$) comprises a poly-T oligonucleotide.

3. The optically labeled perturbation microbead of claim 1, wherein the releasable linkers $L^1$ are independent from the releasable linkers L.

4. The optically labeled perturbation microbead of claim 1, wherein the releasable linkers $L^1$ are different types of linkers from the releasable linkers L.

5. The optically labeled perturbation microbead of claim 1, wherein releasable linker L and releasable linker $L^1$ are different, such that releasable linker L is configured to be cleaved by a first stimulus and the releasable linker $L^1$ is configured to be cleaved by a second stimulus that is different from the first stimulus.

6. The optically labeled perturbation microbead of claim 1, wherein the set of optically detectable labels (W) comprises a set of quantum dots, wherein each quantum dot of the set of quantum dots is configured to generate light of a different wavelength from a remainder of the set of quantum dots.

7. The optically labeled perturbation microbead of claim 1, wherein the set of optically detectable labels (W) comprises a set of micro-components, wherein each micro-component of the set of micro-components is embedded in the perturbation microbead.

8. The optically labeled perturbation microbead of claim 1, wherein each optically detectable label of the set of optically detectable labels (W) is bound to the perturbation microbead (PB) through one or more of an amide bond or an electrostatic attachment.

9. The optically labeled perturbation microbead of claim 1, wherein the set of optically detectable labels (W) comprises optically distinguishable micro-components selected from the group consisting of a set of optically detectable semi-conductor microchips, a set of optically detectable silicon oxide-coated micropucks, and a combination thereof.

10. The optically labeled perturbation microbead of claim 1, wherein the perturbation microbead (PB) is a polystyrene resin bead configured for use in combinatorial library synthesis.

11. The optically labeled perturbation microbead of claim 9, wherein the set of optically detectable labels (W) is attached to the perturbation microbead (PB) and comprises optically detectable labels having a random distribution of different sizes and shapes.

* * * * *